(12) United States Patent
Cunningham

(10) Patent No.: US 6,551,807 B1
(45) Date of Patent: Apr. 22, 2003

(54) CAROTENOID KETOLASE GENES AND GENE PRODUCTS, PRODUCTION OF KETOCAROTENOIDS AND METHODS OF MODIFYING CAROTENOIDS USING THE GENES

(75) Inventor: Francis X. Cunningham, Chevy Chase, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/674,529

(22) PCT Filed: May 21, 1999

(86) PCT No.: PCT/US99/10455

§ 371 (c)(1),
(2), (4) Date: Jul. 23, 2001

(87) PCT Pub. No.: WO99/61652

PCT Pub. Date: Dec. 2, 1999

Related U.S. Application Data

(60) Provisional application No. 60/086,460, filed on May 22, 1998.

(51) Int. Cl.⁷ .............................. C12P 7/26; C12P 23/00; C12N 9/02; C12N 1/20; C07H 21/04

(52) U.S. Cl. ..................... 435/148; 435/67; 435/189; 435/252.3; 435/320.1; 435/410; 435/822; 435/946; 536/23.2

(58) Field of Search .................. 435/148, 67, 189, 435/252.3, 320.1, 822, 946, 410; 536/23.2

(56) References Cited

U.S. PATENT DOCUMENTS

| | | | |
|---|---|---|---|
| 5,453,565 A | 9/1995 | Mawson | 800/200 |
| 5,744,341 A | 4/1998 | Cunningham, Jr. et al. | 435/189 |
| 5,811,273 A | 9/1998 | Misawa et al. | 435/148 |
| 5,910,433 A | 6/1999 | Kajwara et al. | 435/148 |

*Primary Examiner*—Tekchand Saidha
(74) *Attorney, Agent, or Firm*—Arent Fox Kintner Plotkin & Kahn

(57) ABSTRACT

A purified nucleic acid sequence which encodes for a protein having ketolase enzyme activity and has the nucleic acid sequence of SEQ ID NO: 1 or 3, or has a sequence which encodes the amino acid sequence of SEQ ID NO: 2 or 4, as well as vectors and host cells containing them. Methods of use of the nucleic acid sequences to produce ketocarotenoid in host cells and methods of use of the nucleic acid sequences to modify the production of carotenoids in a host cell are included.

20 Claims, 16 Drawing Sheets

FIG.2
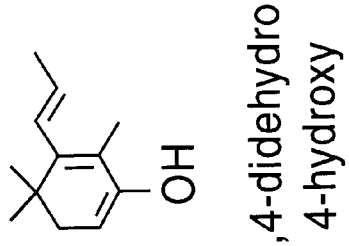
4-keto
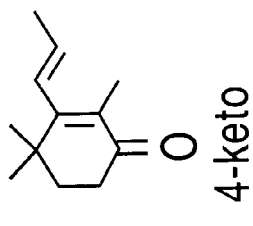
3,4-didehydro 4-hydroxy
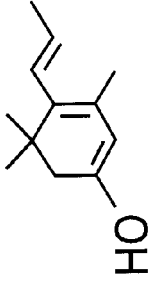
3,4-didehydro
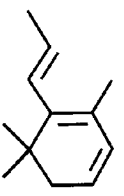
3,4-didehydro 3-hydroxy
ε ring
4-hydroxy
β ring
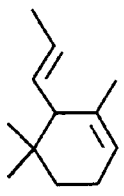
3-hydroxy
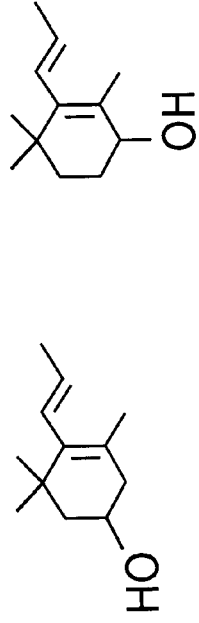

FIG.5
[SEQ ID NO:5]

```
 -23                                       ggg ctgcaggaat tcggcacgag
   1 agcaatctca gtgttcagta caagttattc tttccacaag aatctcttgt
  51 tgcactcaaa acaagacatt ctcaaccgcc catgtttgct cttctctcca
 101 gttgtggtgg agtcgcctat gagaagaaa aagacacatc gtgctgcatg
 151 tatctgctct gttgcagaga gaacaaggaa ccttgatatt cctcaaattg
 201 aagaagagga agagaacgag gaagaactaa tagaacagac ggattctggc
 251 ataattcata taaagaaaac gctagggggg aaacaatcaa gacggtccac
 301 tggctccatt gtcgcacccg tatcttgtct tgggatcctt tcaatgatcg
 351 gacctgctgt ttacttcaag ttttcacggc taatggagtg tggagatatt
 401 cctgtcgcag aaatggggat tacgtttgcc gcctttgttg ctgctgcgat
 451 tggcacggaa tttttgtcag gatgggttca caagaactc tggcacgatt
 501 ctttgtggta cattcacaag tctcaccata ggtcacgaaa aggccgcttc
 551 gagttcaatg atgtgtttgc tattattaac gcgcttcctg ctattgctct
 601 tatcaattat ggattctcaa atgaaggcct ccttcctgga gcctgctttg
 651 gtaccggtct tggaacgaca gtctgtggca tggcttacat ttttcttcac
 701 aatggccttt cacaccgaag gttcccagta gggcttattg caaacgtccc
 751 ttatttccac aagctggctg cagctcacca aatccatcac tcaggaaaat
 801 ttcagggtgt accatttggc ctgttccttg acccccagga attggaagaa
 851 gtaagaggag gcactgaaga attggagagg gtgatcagtc gtacagctaa
 901 acgaacgcaa tcatctacat gaatcaactc ttttacattt atgaggtttt
 951 agtttatcgg tgttacaagt cacacatttg tgtcgttgta gtaattcaaa
1001 gttaccatac tctttttag aattttttt tgatgtatag gtcgcggagt
1051 tacggttaca aaggccaaat ctattgttgt ggaattccat tattaaaaat
1101 aaaaattaga gtttgtagtt ttatctggtg atcaatatca atatatatta
1151 attaaagcaa aaaaaaaaa aaaaaa ctcgag
```

FIG.6

[SEQ ID NO:6]

```
                                                              MGLQEFGTR
aisvfstsys  fhknlllhsk  qdilnrpcll  fspvvvespm  rkkkthraac
icsvaertrn  ldipqieeee  eneeelieqt  dsgiihikkt  lggkqsrrst
gsivapvscl  gilsmigpav  yfkfsrlmec  gdipvaemgi  tfaafvaaai
gteflsgwvh  kelwhdslwy  ihkshhrsrk  grfefndvfa  iinalpaial
inygfsnegl  lpgacfgtgl  gttvcgmayi  flhnglshrr  fpvglianvp
yfhklaaahq  ihhsgkfqgv  pfglflgpqe  leevrggtee  lervisrtak
rtqsst*
```

FIG.7
[SEQ ID NO:7]

```
                                      ggg ctgcaggaat tcggcacgag
-23
   1 agcaatttca gtgttcagtt caggttattc tttctacaag aatctcttgt
  51 tggactcaaa accaaatatt ctcaaacccc catgcctgct attctctcca
 101 gttgtgatca tgtcgcctat gagaagaaa  aagaaacatg gtgatccatg
 151 tatctgctcc gttgcaggga gaacaaggaa ccttgatatt cctcaaattg
 201 aagaagagga agagaatgtg gaagaactaa tagaacagac cgattctgac
 251 atagtgcata taaagaaaac actaggggggg aaacaatcaa aacggcccac
 301 tggctccatt gtcgcacccg tatcttgtct tgggatcctt tcaatgattg
 351 gacctgctgt ttacttcaag ttttcacggc taatggaggg tggagatata
 401 cctgtagcag aaatggggat tacgtttgcc acctttgttg ctgctgctgt
 451 tggcacggag tttttgtcag catgggttca caaagaactc tggcacgagt
 501 ctttgtggta cattcacaag tctcaccatc ggtcacgaaa aggccgcttc
 551 gagttcaatg atgtgtttgc tattattaac gcgcttcccg ctattgctct
 601 tatcaattat ggattctcca atgaaggcct ccttcctgga gcgtgctttg
 651 gtgtcggtct tggaacaaca gtctgtggta tggcttacat ttttcttcac
 701 aatggcctat cacaccgaag gttcccagta tggcttattg cgaacgtccc
 751 ttatttccac aagctggctg cagctcacca aatacaccac tcaggaaaat
 801 ttcagggtgt accatttggc ctgttccttg gacccaagga attggaagaa
 851 gtaagaggag gcactgaaga gttggagagg gtaatcagtc gtacaactaa
 901 acgaacgcaa ccatctacct gaatcaattt ttttacatat ataaggtttt
 951 agtttatcgg tgttataaaa tcacacatcc gtatcgtttt agtaagtcaa
1001 agttaagata cttccttctt agaatatttt ttgatgtata ggtcgcggat
1051 atactgttac actattcgtt gtggaattcc attataaaaa ataaaaaaa
1101 aaaaaaaaaa aa ctcgag
```

FIG. 8
[SEQ ID NO:8]

```
                                                            MGLQEFGTR
aisvfssgys fyknllldsk pnilkppcll fspvvimspm rkkkkhgdpc
icsvagrtrn ldipqieeee enveelieqt dsdivhikkt lggkqskrpt
gsivapvscl gilsmigpav yfkfsrlmeg gdipvaemgi tfatfvaaav
gteflsawvh kelwheslwy ihkshhrsrk grfefndvfa iinalpaial
inygfsnegl lpgacfgvgl gttvcgmayi flhnglshrr fpvwlianvp
yfhklaaahq ihhsgkfqgv pfglflgpke leevrggtee lervisrttk
rtqpst*
```

FIG.9A
GAP OF SEQ ID NO:9
AND SEQ ID NO:3

```
  1 agcaatctcagtgttcagtacaagttattctttccacaagaatctcttgt  50
    ||||||  ||||||||||||| || ||||||||||| |||||||||||||
  1 agcaatttcagtgttcagttcaggttattctttctacaagaatctcttgt  50

51 tgcactcaaaacaagacattctcaaccgcccatgtttgctcttctctcca 100
    || ||||||||| |  | ||||||||  |||||| ||||  |||||||||
 51 tggactcaaaaccaaatattctcaaccccc atgcctgctattctctcca 100

101 gttgtggtggagtcgcctatgagaaagaaaaagacacatcgtgctgcatg 150
    ||||||  |       ||||||||||||||||||| |||| ||| | ||||
101 gttgtgatcatgtcgcctatgagaaagaaaaagaaacatggtgatccatg 150

151 tatctgctctgttgcagagagaacaaggaaccttgatattcctcaaattg 200
    |||||||| ||||||| |||||||||||||||||||||||||||||||||
151 tatctgctccgttgcagggagaacaaggaaccttgatattcctcaaattg 200

201 aagaagaggaagagaacgaggaagaactaatagaacagacggaftctggc 250
    ||||||||||||||| | ||||||||||||||||||||||| ||||| |
201 aagaagaggaagagaatgtggaagaactaatagaacagaccgattctgac 250

251 ataattcatataaagaaaacgctagggggaaacaatcaagacggtccac 300
    ||| | ||||||||||||| |||||||||||||||||||| |||| ||||
251 atagtgcatataaagaaaacactagggggaaacaatcaaaacggcccac 300

301 tggctccattgtcgcacccgtatcttgtcttgggatcctttcaatgatcg 350
    |||||||||||||||||||||||||||||||||||||||||||||||| |
301 tggctccattgtcgcacccgtatcttgtcttgggatcctttcaatgattg 350
```

FIG.9B

```
351 gacctgctgtttacttcaagttttcacggctaatggagtgtggagatatt 400
    ||||||||||||||||||||||||||||||||||||||| ||||||||||
351 gacctgctgtttacttcaagttttcacggctaatggagggtggagatata 400

401 cctgtcgcagaaatggggattacgtttgccgcctttgttgctgctgcgat 450
    |||||  ||||||||||||||||||||||||| ||||||||||||||| |
401 cctgtagcagaaatggggattacgtttgccacctttgttgctgctgctgt 450

451 tggcacggaattttgtcaggatgggttcacaaagaactctggcacgatt 500
    |||||||| |||||||| ||||||||||||||||||||||||||||| |
451 tggcacggagttttgtcagcatgggttcacaaagaactctggcacgagt 500

501 ctttgtggtacattcacaagtctcaccataggtcacgaaaaggccgcttc 550
    |||||||||||||||||||||||||||||| |||||||||||||||||||
501 ctttgtggtacattcacaagtctcaccatcggtcacgaaaaggccgcttc 550

551 gagttcaatgatgtgtttgctattattaacgcgcttcctgctattgctct 600
    |||||||||||||||||||||||||||||||||||| |||||||||||||
551 gagttcaatgatgtgtttgctattattaacgcgcttcccgctattgctct 600

601 tatcaattatggattctcaaatgaaggcctccttcctggagcctgctttg 650
    ||||||||||||||||| |||||||||||||||||||||||| |||||||
601 tatcaattatggattctccaatgaaggcctccttcctggagcgtgctttg 650

651 gtaccggtcttggaacgacagtctgtggcatggcttcattttcttcac 700
    ||  ||||||||||| |||||||||| ||||||||||||||||||||||
651 gtgtcggtcttggaacaacagtctgtggtatggcttacattttcttcac 700
```

FIG.9C

```
701 aatggcctttcacaccgaaggttcccagtagggcttattgcaaacgtccc 750
    ||||||||  |||||||||||||||||||| |||||||||| ||||||||
701 aatggcctatcacaccgaaggttcccagtatggcttattgcgaacgtccc 750

751 ttatttccacaagctggctgcagctcaccaaatccatcactcaggaaaat 800
    |||||||||||||||||||||||||||||||||    |||||||||||||
751 ttatttccacaagctggctgcagctcaccaaatacaccactcaggaaaat 800

801 ttcagggtgtaccatttggcctgttccttggaccccaggaattggaagaa 850
    ||||||||||||||||||||||||||||||||||| ||||||||||||||
801 ttcagggtgtaccatttggcctgttccttggacccaaggaattggaagaa 850

851 gtaagaggaggcactgaagaattggagagggtgatcagtcgtacagctaa 900
    |||||||||||||||||||||||| ||||||||||| ||||||||| |||
851 gtaagaggaggcactgaagagttggagagggtaatcagtcgtacaactaa 900

901 acgaacgcaatcatctacaTGAatcaactcttttacatttatgaggtttt 950
    ||||||||| |||||| ||||||||| | ||||||||| ||| |||||||
901 acgaacgcaaccatctaccTGAatcaatttttttacatatataaggtttt 950

951 agtttatcggtgtta.caagtcacacatttgtgtcgttgtagtaattcaa 999
    ||||||||||||||  || ||||||||  || ||||| |||||| ||||
 951 agtttatcggtgttataaaatcacacatccgtatcgttttagtaagtcaa 1000

1000 agttaccatactctttttagaatttttttttgatgtataggtcgcggag 1049
     |||||  |||||  || |    | |  ||||||||||||||||||||||
1001 agttaagatacttccttcttagaatattttttgatgtataggtcgcggat 1050
```

FIG.9D

```
     .         .         .         .         .
1050 ttacggttacaaaggccaaatctattgttgtggaattccattattaaaaa 1099
     ||| |||||           |         ||||||||||||||| |||||
1051 atactgttac.........actattcgttgtggaattccattataaaaaa 1091

.         .         .         .         .
1100 taaaaattagagtttgtagttttatctggtgatcaatatcaatatatatt 1149
         ||||  | |
1092 ataaaaaaaaaaaaaaaaaa
```

FIG.10

GAP OF SEQ ID NO:2 AND SEQ ID NO:4

```
  1 AISVFSTSYSFHKNLLLHSKQDILNRPCLLFSPVVVESPMRKKKTHRAAC  50
    ||||||.|||:|||||||.||||||||||:|||||||||
  1 AISVFSSGYSFYKNLLLDSKPNILKPPCLLFSVVIMSPMRKKKKHGDPC  50

51 ICSVAERTRNLDIPQIEEEEENEEELIEQTDSGIIHIKKTLGGKQSRRST 100
    |||||.|||||||||||||||.||||||||.|:|||||||||||:|.|
 51 ICSVAGRTRNLDIPQIEEEEENVEELIEQTDSDIVHIKKTLGGKQSKRPT 100

101 GSIVAPVSCLGILSMIGPAVYFKFSRLMECGDIPVAEMGITFAAFVAAAI 150
    ||||||||||||||||||||||||||||.|||||||||||||.|||||:
101 GSIVAPVSCLGILSMIGPAVYFKFSRLMEGGDIPVAEMGITFATFVAAAV 150

151 GTEFLSGWVHKELWHDSLWYIHKSHHRSRKGRFEFNDVFAIINALPAIAL 200
    ||||||.|||||||:||||||||||||||||||||||||||||||||||
151 GTEFLSAWVHKELWHESLWYIHKSHHRSRKGRFEFNDVFAIINALPAIAL 200

201 INYGFSNEGLLPGACFGTGLGTTVCGMAYIFLHNGLSHRRFPVGLIANVP 250
    ||||||||||||||||||.||||||||||||||||||||||||.||||||
201 INYGFSNEGLLPGACFGVGLGTTVCGMAYIFLHNGLSHRRFPVWLIANVP 250

251 YFHKLAAAHQIHHSGKFQGVPFGLFLGPQELEEVRGGTEELERVISRTAK 300
    |||||||||||||||||||||||||||.||||||||||||||||||||.|
251 YFHKLAAAHQIHHSGKFQGVPFGLFLGPKELEEVRGGTEELERVISRTTK 300

301 RTQSST* 307
    |||.|||
301 RTQPST* 307
```

FIG. 11

GAP OF SEQ ID NO:2 AND ARABIDOPSIS
β-CAROTENE HYDROXYLASE (SEQ ID NO:10)

```
  1 AISVFSTSYSFHKNLLLHSKQDILNRPCLLFSPVVVESPMRKKKTHRAAC  50
     ||..|     ||      ||   .    ||  .     :  |.
  1 MAAXLSTAVTFKP...LHRSFSSSSTDFRLRLPKSLSGFSPSLRFKRFSV  47

51 ICSVAERTRNLDIPQIEEEEENEEELIEQTDSGIIHIKKTLGGKQSRRST 100
    | ||.|  |  | |     |      :  ::.|  |.| |||
 48 CYVVEERRQNSPIENDERPESTSSTNAIDAEYLALRLAEKLERKKSERST  97

101 GSIVAPVSCLGILSMIGPAVYFKFSRLMECGDIPVAEMGITFAAFVAAAI 150
    | | .|  || ||    |||::||   || |:|. ||   ||| | ||:
 98 YLIAAMLSSFGITSMAVMAVYYRFSWQMEGGEISMLEMFGTFALSVGAAV 147

151 GTEFLSGWVHKELWHDSLWYIHKSHHRSRKGRFEFNDVFAIINALPAIAL 200
    | || . | |: ||| |||  .|.|||: |.| || ||||||:|| ||| |
148 GMEFWARWAHRALWHASLWNMHESHHKPREGPFELNDVFAIVNAGPAIGL 197

201 INYGFSNEGLLPGACFGTGLGTTVCGMAYIFLHNGLSHRRFPVGLIANVP 250
    :.|||  |.||.|| || ||| ||| |.||.|.|.|| |:|||||  ||.||
198 LSYGFFNKGLVPGLCFGAGLGITVFGIAYMFVHDGLVHKRFPVGPIADVP 247

251 YFHKLAAAHQIHHSGKFQGVPFGLFLGPQELEEVRGGTEELERVISRTAK 300
    |  |.||||:||. || |||:||||||.||||| || |||::  |||  |
248 YLRKVAAAHQLHHTDKFNGVPYGLFLGPKELEEV.GGNEELDKEISRRIK 296

301 RTQSST*........ 307
    . ..
297 SYKKASGSGSSSSS* 311
```

FIG.12A (SEQ ID NO: 11)

```
 1 CATACCATAA ATAGTAGAGG ACAACCTACA AACCAACCAC CAGAAACCTC 50
51 CAATGGCAGC
```

FIG.12B (SEQ ID NO: 12)

MAAAISVFSSGYSFYKNLLLDSKPNILKPPCLLFSPVVIMSPMRKKKKHGDPCICSVAGR
TRNLDIPQIEEEEENVEELIEQTDSDIVHIKKTLGGKQSKRPTGSIVAPVSCLGILSMIG
PAVYFKFSRLMEGGDIPVAEMGITFATFVAAAVGTEFLSAWVHKELWHESLWYIHKSHHR
SRKGRFEFNDVFAIINALPAIALINYGFSNEGLLPGACFGVGLGTTVCGMAYIFLHNGLS
HRRFPVWLIANVPYFHKLAAAHQIHHSGKFQGVPFGLFLGPKELEEVRGGTEELERVISR
TTKRTQPST*

Fig. 13

```
              *         20         *         40         *         60         *
At1   : ------------MAAXLSTAVTFKPLHRSFSSSSTDFRLRLPKslsgfspslR----------fkrfsvcyvve :  52
At2   : ------------------MAAGLSTIAVTLKPLNRSSFSANHPIstavfppslRFNGFRR----rkiltvcfvve :  53
Ca1   : ------------MAAEISISASSRAICLQRNPFPAPKYFATAPpllffspltCNLDAILRSRRkprlaacfvlk :  62
Ca2   : TTGRYHYQLVWCQISFSSTSRTSYYRHSPFLGPKPTPTTPSVYpitpfspnlGSILRCRR---rpsitvcfvle :  71
AdK1  : ------------------AISVFSTSYSFHKNLLLHSKQDILNRpcllfspvvVESPMRKKKT-hraacicsvae :  56
AdK6  : ------------MAAAISVFSSGYSFYKNLLLDSKPNILKPpcllfspvvIMSPMRKKKK-hgdpcicsvag :  59
                                               s                  FsP          C V 80         *        100         *        120         *        140
At1   : errqNSPIENDERPESTSSTNAIDAEYLAL----rlaeklekkserstyliaamlssfgitsmavmavyyrfs : 122
At2   : erkqSSPMDDDNKPESTTSSSEILMTS-------rllkkaekkkserftyliaavmssfgitsmaimavyyrfs : 120
Ca1   : ddklYTAQSGKQSDTEAIGDEIEVETNEEKSLAVrlaekfarkkserftylvaavmsslgitsmavisvyyrfs : 136
Ca2   : ddkfKTQFEAGEEDIEMKIEEQISAT--------rlaeklarkkserftylvaaymssfgitsmavmavyyrfy : 137
AdK1  : rtrnlDIPQIEEEEENEEELIEQTDSGII-----hikktlggkqsrrstgsivapvsdlgilsmigpavyfkfs : 125
AdK6  : rtrnlDIPQIEEEEENVEELIEQTDSDIV-----hikktlggkqskrptgsivapvsdlgilsmigpavyfkfs : 128
                                               K S R T   A    S  GI SM   aVY Fs

*        160         *        180         *        200         *        220
At1   : wqmeggeismlemfgtfalsvg-aavgmefwarwahralwhaslwnmmheshhkpregpfelndvfaivnagpai : 195
At2   : wqmkggevsvlemfgtfalsVgaavvgmefwarwahralwhdslwnmmheshhkpregafelndvfaitnavpai : 194
Ca1   : wqmeggempfsemfctfalafg-aaigmeywarwahralwhaslwhmmheshhrpregpfelndifaiinavpai : 209
Ca2   : wqmeggevpfsemfgtfalsvg-aavgmefwarwahkalwhaslwhmmheshhkpregpfelndvfaiinavpai : 210
AdK1  : rlmecgdipvaemgitfaalva-aaigteflsgwvhkelwhdslwyihkshhrsrkgrfefndvfaiinalpai : 198
AdK6  : rlmeggdipvaemgitfatfva-aavgteflsawvhkelwheslwyihkshhrsrkgrfefndvfaiinalpai : 201
              MegG    EM  TFA  v Aa G Ef     W H LWH SLW  H SHH  R G FE NDvFAI NA PAI

*        240         *        260         *        280         *
At1   : gllsygffnkglvpglcfgaglgitvfgiaymfvhdglvhkrfpvggiadvpylrkyaaahqlhhtdkfngvpy : 269
At2   : gllyygflnkglvpglcfgaglgitmfgmaymfvhdglvhkrfpvgpianvpylrkyaaahqlhhtdkfdgvpy : 268
Ca1   : affsfgfnhkglipglcfgaglgitvfgmaymfvhdglvhkrfpvgpiakvpyfqryaaahqlhhsdkfdgvpy : 283
Ca2   : alldygffhkglipglcfgaglgitvfgmaymfvhdglvhkrfpvgpianvpylrkyaaahslhhsekfngvpy : 284
AdK1  : alinygfsneglipgacfgtglgttvcgmayiflhnglshkrfpvglianvpyfhklaaahqlhhsgkfqgvpy : 272
AdK6  : alinygfsneglipgacfgvglgttvcgmayiflhnglshkrfpvwlianvpyfhklaaahqlhhsgkfqgvpf : 275
                l  yGF  GL PG CFG GLG Tv GmAY F  H GL H RFPVg iA VPY  k AAAHq HH  KF GVP 300         *        320         *
At1   : glflgpkeleevgg-neeldkeisrriksykkaSGSGSSSSS : 310
At2   : glflgpkqeveevgKkeelekeisrriklynkgSSTS----- : 305
Ca1   : glflgpkeleevgv-ieelekevnrriksikrl--------- : 315
Ca2   : glflgpkeleevgg-leelekevnrrtryikgs--------- : 316
AdK1  : glflgpqeleevrgGteelervisrrakrtqssT-------- : 306
AdK6  : glflgpkeleevrgGteelervisrrtkrtqpsT-------- : 309
         GLFLGPkeleEv g  EELe   R   k
```

SEQUENCE LISTING

<160> NUMBER OF SEQ ID NOS: 18

<210> SEQ ID NO 1
<211> LENGTH: 1176
<212> TYPE: DNA
<213> ORGANISM: Adonis aestivalis

<400> SEQUENCE: 1

```
agcaatctca gtgttcagta caagttattc tttccacaag aatctcttgt tgcactcaaa      60
acaagacatt ctcaaccgcc catgtttgct cttctctcca gttgtggtgg agtcgcctat     120
gagaaagaaa aagacacatc gtgctgcatg tatctgctct gttgcagaga gaacaaggaa     180
```

-continued

```
ccttgatatt cctcaaattg aagaagagga agagaacgag gaagaactaa tagaacagac    240
ggattctggc ataattcata taaagaaaac gctagggggg aaacaatcaa gacggtccac    300
tggctccatt gtcgcacccg tatcttgtct tgggatcctt tcaatgatcg gacctgctgt    360
ttacttcaag ttttcacggc taatggagtg tggagatatt cctgtcgcag aaatggggat    420
tacgtttgcc gcctttgttg ctgctgcgat tggcacggaa ttttttgtcag gatgggttca    480
caaagaactc tggcacgatt ctttgtggta cattcacaag tctcaccata ggtcacgaaa    540
aggccgcttc gagttcaatg atgtgttttgc tattattaac gcgcttcctg ctattgctct    600
tatcaattat ggattctcaa atgaaggcct ccttcctgga gcctgctttg gtaccggtct    660
tggaacgaca gtctgtggca tggcttacat ttttcttcac aatggccttt cacaccgaag    720
gttcccagta gggcttattg caaacgtccc ttatttccac aagctggctg cagctcacca    780
aatccatcac tcaggaaaat ttcagggtgt accatttggc ctgttccttg accccagga    840
attggaagaa gtaagaggag gcactgaaga attggagagg gtgatcagtc gtacagctaa    900
acgaacgcaa tcatctacat gaatcaactc ttttacattt atgaggtttt agtttatcgg    960
tgttacaagt cacacatttg tgtcgttgta gtaattcaaa gttaccatac tctttttag   1020
aattttttt tgatgtatag gtcgcggagt tacggttaca aaggccaaat ctattgttgt   1080
ggaattccat tattaaaaat aaaaattaga gtttgtagtt ttatctggtg atcaatatca   1140
atatatatta attaaagcaa aaaaaaaaaa aaaaaa                             1176
```

<210> SEQ ID NO 2
<211> LENGTH: 306
<212> TYPE: PRT
<213> ORGANISM: Adonis aestivalis

<400> SEQUENCE: 2

```
Ala Ile Ser Val Phe Ser Thr Ser Tyr Ser Phe His Lys Asn Leu Leu
1               5                   10                  15

Leu His Ser Lys Gln Asp Ile Leu Asn Arg Pro Cys Leu Leu Phe Ser
            20                  25                  30

Pro Val Val Glu Ser Pro Met Arg Lys Lys Thr His Arg Ala
        35                  40                  45

Ala Cys Ile Cys Ser Val Ala Glu Arg Thr Arg Asn Leu Asp Ile Pro
    50                  55                  60

Gln Ile Glu Glu Glu Glu Asn Glu Glu Leu Ile Glu Gln Thr
65                  70                  75                  80

Asp Ser Gly Ile Ile His Ile Lys Lys Thr Leu Gly Gly Lys Gln Ser
                85                  90                  95

Arg Arg Ser Thr Gly Ser Ile Val Ala Pro Val Ser Cys Leu Gly Ile
            100                 105                 110

Leu Ser Met Ile Gly Pro Ala Val Tyr Phe Lys Phe Ser Arg Leu Met
        115                 120                 125

Glu Cys Gly Asp Ile Pro Val Ala Glu Met Gly Ile Thr Phe Ala Ala
    130                 135                 140

Phe Val Ala Ala Ala Ile Gly Thr Glu Phe Leu Ser Gly Trp Val His
145                 150                 155                 160

Lys Glu Leu Trp His Asp Ser Leu Trp Tyr Ile His Lys Ser His His
                165                 170                 175

Arg Ser Arg Lys Gly Arg Phe Glu Phe Asn Asp Val Phe Ala Ile Ile
            180                 185                 190
```

```
Asn Ala Leu Pro Ala Ile Ala Leu Ile Asn Tyr Gly Phe Ser Asn Glu
            195                 200                 205

Gly Leu Leu Pro Gly Ala Cys Phe Gly Thr Gly Leu Gly Thr Thr Val
            210                 215                 220

Cys Gly Met Ala Tyr Ile Phe Leu His Asn Gly Leu Ser His Arg Arg
225                 230                 235                 240

Phe Pro Val Gly Leu Ile Ala Asn Val Pro Tyr Phe His Lys Leu Ala
                245                 250                 255

Ala Ala His Gln Ile His His Ser Gly Lys Phe Gln Gly Val Pro Phe
                260                 265                 270

Gly Leu Phe Leu Gly Pro Gln Glu Leu Glu Glu Val Arg Gly Gly Thr
            275                 280                 285

Glu Glu Leu Glu Arg Val Ile Ser Arg Thr Ala Lys Arg Thr Gln Ser
290                 295                 300

Ser Thr
305

<210> SEQ ID NO 3
<211> LENGTH: 1112
<212> TYPE: DNA
<213> ORGANISM: Adonis aestivalis

<400> SEQUENCE: 3
agcaatttca gtgttcagtt caggttattc tttctacaag aatctcttgt tggactcaaa      60
accaaatatt ctcaaacccc catgcctgct attctctcca gttgtgatca tgtcgcctat     120
gagaaagaaa aagaaacatg gtgatccatg tatctgctcc gttgcaggga gaacaaggaa     180
ccttgatatt cctcaaattg aagaaggaga agagaatgtg gaagaactaa tagaacagac     240
cgattctgac atagtgcata taagaaaaac actagggggg aaacaatcaa acggcccac      300 tggctccatt gtcgcacccg tatcttgtct tgggatcctt tcaatgattg acctgctgt      360 ttacttcaag ttttcacggc taatggaggg tggagatata cctgtagcag aaatggggat     420
tacgtttgcc acctttgttg ctgctgctgt tggcacggga ttttgtcag catgggttca     480 caaagaactc tggcacgagt ctttgtggta cattcacaag tctcaccatc ggtcacgaaa     540
aggccgcttc gagttcaatg atgtgtttgc tattattaac gcgcttcccg ctattgctct     600
tatcaattat ggattctcca atgaaggcct ccttcctgga gcgtgctttg gtgtcggtct     660
tggaacaaca gtctgtggta tggcttacat ttttcttcac aatggcctat cacaccgaag     720
gttcccagta tggcttattg cgaacgtccc ttatttccac aagctggctg cagctcacca     780
aatacaccac tcaggaaaat ttcagggtgt accatttggc ctgttccttg acccaaggta     840
attggaagaa gtaagaggag gcactgaaga gttggagagg gtaatcagtc gtacaactaa     900
acgaacgcaa ccatctacct gaatcaattt ttttacatat ataaggtttt agtttatcgg     960
tgttataaaa tcacacatcc gtatcgtttt agtaagtcaa agttaagata cttccttctt    1020
agaatatttt tgatgtata ggtcgcggat atactgttac actattcgtt gtggaattcc    1080
attataaaaa aataaaaaaa aaaaaaaaa aa                                   1112

<210> SEQ ID NO 4
<211> LENGTH: 306
<212> TYPE: PRT
<213> ORGANISM: Adonis aestivalis

<400> SEQUENCE: 4

Ala Ile Ser Val Phe Ser Ser Gly Tyr Ser Phe Tyr Lys Asn Leu Leu
```

```
  1               5                   10                  15
Leu Asp Ser Lys Pro Asn Ile Leu Lys Pro Pro Cys Leu Leu Phe Ser
                20                  25                  30
Pro Val Val Ile Met Ser Pro Met Arg Lys Lys Lys His Gly Asp
            35                  40                  45
Pro Cys Ile Cys Ser Val Ala Gly Arg Thr Arg Asn Leu Asp Ile Pro
        50                  55                  60
Gln Ile Glu Glu Glu Glu Asn Val Glu Glu Leu Ile Glu Gln Thr
65                  70                  75                  80
Asp Ser Asp Ile Val His Ile Lys Lys Thr Leu Gly Gly Lys Gln Ser
                85                  90                  95
Lys Arg Pro Thr Gly Ser Ile Val Ala Pro Val Ser Cys Leu Gly Ile
            100                 105                 110
Leu Ser Met Ile Gly Pro Ala Val Tyr Phe Lys Phe Ser Arg Leu Met
            115                 120                 125
Glu Gly Gly Asp Ile Pro Val Ala Glu Met Gly Ile Thr Phe Ala Thr
    130                 135                 140
Phe Val Ala Ala Val Gly Thr Glu Phe Leu Ser Ala Trp Val His
145                 150                 155                 160
Lys Glu Leu Trp His Glu Ser Leu Trp Tyr Ile His Lys Ser His His
                165                 170                 175
Arg Ser Arg Lys Gly Arg Phe Glu Phe Asn Asp Val Phe Ala Ile Ile
            180                 185                 190
Asn Ala Leu Pro Ala Ile Ala Leu Ile Asn Tyr Gly Phe Ser Asn Glu
            195                 200                 205
Gly Leu Leu Pro Gly Ala Cys Phe Gly Val Gly Leu Gly Thr Thr Val
    210                 215                 220
Cys Gly Met Ala Tyr Ile Phe Leu His Asn Gly Leu Ser His Arg Arg
225                 230                 235                 240
Phe Pro Val Trp Leu Ile Ala Asn Val Pro Tyr Phe His Lys Leu Ala
                245                 250                 255
Ala Ala His Gln Ile His His Ser Gly Lys Phe Gln Gly Val Pro Phe
            260                 265                 270
Gly Leu Phe Leu Gly Pro Lys Glu Leu Glu Glu Val Arg Gly Gly Thr
        275                 280                 285
Glu Glu Leu Glu Arg Val Ile Ser Arg Thr Thr Lys Arg Thr Gln Pro
    290                 295                 300
Ser Thr
305

<210> SEQ ID NO 5
<211> LENGTH: 1205
<212> TYPE: DNA
<213> ORGANISM: Adonis aestivalis

<400> SEQUENCE: 5
gggctgcagg aattcggcac gagagcaatc tcagtgttca gtacaagtta ttctttccac    60
aagaatctct tgttgcactc aaaacaagac attctcaacc gcccatgttt gctcttctct   120
ccagttgtgg tggagtcgcc tatgagaaag aaaaagacac atcgtgctgc atgtatctgc   180
tctgttgcag agagaacaag gaaccttgat attcctcaaa ttgaagaaga ggaagagaac   240
gaggaagaac taatagaaca gacggattct ggcataattc atataaagaa aacgctaggg   300
gggaaacaat caagacggtc cactggctcc attgtcgcac ccgtatcttg tcttgggatc   360
```

-continued

```
ctttcaatga tcggacctgc tgtttacttc aagttttcac ggctaatgga gtgtggagat      420
attcctgtcg cagaaatggg gattacgttt gccgcctttg ttgctgctgc gattggcacg      480 gaattttgt caggatgggt tcacaaagaa ctctggcacg attctttgtg gtacattcac       540
aagtctcacc ataggtcacg aaaaggccgc ttcgagttca atgatgtgtt tgctattatt     600
aacgcgcttc ctgctattgc tcttatcaat tatggattct caaatgaagg cctccttcct     660
ggagcctgct ttggtaccgg tcttggaacg acagtctgtg gcatggctta cattttcttt    720
cacaatggcc tttcacaccg aaggttccca gtagggctta tgcaaacgt cccttatttc      780 cacaagctgg ctgcagctca ccaaatccat cactcaggaa aatttcaggg tgtaccattt    840
ggcctgttcc ttgacccca ggaattggaa gaagtaagag gaggcactga agaattggag      900
agggtgatca gtcgtacagc taaacgaacg caatcatcta catgaatcaa ctcttttaca     960
tttatgaggt tttagtttat cggtgttaca agtcacacat ttgtgtcgtt gtagtaattc    1020
aaagttacca tactcttttt tagaattttt ttttgatgta taggtcgcgg agttacggtt    1080
acaaaggcca aatcattgt tgtggaattc cattattaaa aataaaaatt agagtttgta     1140
gttttatctg gtgatcaata tcaatatata ttaattaaag caaaaaaaa aaaaaaaac     1200 tcgag                                                                1205
```

<210> SEQ ID NO 6
<211> LENGTH: 315
<212> TYPE: PRT
<213> ORGANISM: Adonis aestivalis

<400> SEQUENCE: 6

```
Met Gly Leu Gln Glu Phe Gly Thr Arg Ala Ile Ser Val Phe Ser Thr
1               5                   10                  15

Ser Tyr Ser Phe His Lys Asn Leu Leu Leu His Ser Lys Gln Asp Ile
            20                  25                  30

Leu Asn Arg Pro Cys Leu Leu Phe Ser Pro Val Val Glu Ser Pro
        35                  40                  45

Met Arg Lys Lys Lys Thr His Arg Ala Ala Cys Ile Cys Ser Val Ala
    50                  55                  60

Glu Arg Thr Arg Asn Leu Asp Ile Pro Gln Ile Glu Glu Glu Glu
65                  70                  75                  80

Asn Glu Glu Glu Leu Ile Glu Gln Thr Asp Ser Gly Ile Ile His Ile
                85                  90                  95

Lys Lys Thr Leu Gly Gly Lys Gln Ser Arg Arg Ser Thr Gly Ser Ile
            100                 105                 110

Val Ala Pro Val Ser Cys Leu Gly Ile Leu Ser Met Ile Gly Pro Ala
        115                 120                 125

Val Tyr Phe Lys Phe Ser Arg Leu Met Glu Cys Gly Asp Ile Pro Val
    130                 135                 140

Ala Glu Met Gly Ile Thr Phe Ala Ala Phe Val Ala Ala Ile Gly
145                 150                 155                 160

Thr Glu Phe Leu Ser Gly Trp Val His Lys Glu Leu Trp His Asp Ser
                165                 170                 175

Leu Trp Tyr Ile His Lys Ser His His Arg Ser Arg Lys Gly Arg Phe
            180                 185                 190

Glu Phe Asn Asp Val Phe Ala Ile Ile Asn Ala Leu Pro Ala Ile Ala
        195                 200                 205

Leu Ile Asn Tyr Gly Phe Ser Asn Glu Gly Leu Leu Pro Gly Ala Cys
    210                 215                 220
```

Phe Gly Thr Gly Leu Gly Thr Thr Val Cys Gly Met Ala Tyr Ile Phe
225                 230                 235                 240

Leu His Asn Gly Leu Ser His Arg Arg Phe Pro Val Gly Leu Ile Ala
            245                 250                 255

Asn Val Pro Tyr Phe His Lys Leu Ala Ala Ala His Gln Ile His His
            260                 265                 270

Ser Gly Lys Phe Gln Gly Val Pro Phe Gly Leu Phe Leu Gly Pro Gln
            275                 280                 285

Glu Leu Glu Glu Val Arg Gly Gly Thr Glu Glu Leu Glu Arg Val Ile
        290                 295                 300

Ser Arg Thr Ala Lys Arg Thr Gln Ser Ser Thr
305                 310                 315

<210> SEQ ID NO 7
<211> LENGTH: 1141
<212> TYPE: DNA
<213> ORGANISM: Adonis aestivalis

<400> SEQUENCE: 7
gggctgcagg aattcggcac gagagcaatt tcagtgttca gttcaggtta ttctttctac      60
aagaatctct tgttggactc aaaccaaat attctcaaac ccccatgcct gctattctct     120
ccagttgtga tcatgtcgcc tatgagaaag aaaagaaac atggtgatcc atgtatctgc     180
tccgttgcag ggagaacaag gaaccttgat attcctcaaa ttgaagaaga ggaagagaat     240
gtggaagaac taatagaaca gaccgattct gacatagtgc atataaagaa aacactaggg     300
gggaaacaat caaaacggcc cactggctcc attgtcgcac ccgtatcttg tcttgggatc     360
cttcaatga ttggacctgc tgtttacttc aagttttcac ggctaatgga gggtggagat     420
atacctgtag cagaaatggg gattacgttt gccacctttg ttgctgctgc tgttggcacg     480
gagttttgt cagcatgggt tcacaaagaa ctctggcacg agtctttgtg gtacattcac     540
aagtctcacc atcggtcacg aaaaggccgc ttcgagttca atgatgtgtt tgctattatt     600
aacgcgcttc ccgctattgc tcttatcaat tatggattct ccaatgaagg cctccttcct     660
ggagcgtgct ttggtgtcgg tcttggaaca acagtctgtg gtatggctta cattttctt     720
cacaatggcc tatcacaccg aaggttccca gtatggctta ttgcgaacgt cccttatttc     780
cacaagctgg ctgcagctca ccaaatacac cactcaggaa aatttcaggg tgtaccattt     840
ggcctgttcc ttggacccaa ggaattggaa gaagtaagag gaggcactga agagttggag     900
agggtaatca gtcgtacaac taaacgaacg caaccatcta cctgaatcaa ttttttttaca     960
tatataaggt tttagtttat cggtgttata aaatcacaca tccgtatcgt tttagtaagt    1020
caaagttaag atacttcctt cttagaatat tttttgatgt ataggtcgcg gatatactgt    1080
tacactattc gttgtggaat tccattataa aaaataaaa aaaaaaaaa aaaaactcga    1140
g                                                                  1141

<210> SEQ ID NO 8
<211> LENGTH: 315
<212> TYPE: PRT
<213> ORGANISM: Adonis aestivalis

<400> SEQUENCE: 8

Met Gly Leu Gln Glu Phe Gly Thr Arg Ala Ile Ser Val Phe Ser Ser
1               5                   10                  15

Gly Tyr Ser Phe Tyr Lys Asn Leu Leu Leu Asp Ser Lys Pro Asn Ile

```
                     20                  25                  30
Leu Lys Pro Pro Cys Leu Leu Phe Ser Pro Val Val Ile Met Ser Pro
         35                  40                  45
Met Arg Lys Lys Lys His Gly Asp Pro Cys Ile Cys Ser Val Ala
 50                  55                  60
Gly Arg Thr Arg Asn Leu Asp Ile Pro Gln Ile Glu Glu Glu Glu
 65                  70                  75                  80
Asn Val Glu Glu Leu Ile Glu Gln Thr Asp Ser Asp Ile Val His Ile
                 85                  90                  95
Lys Lys Thr Leu Gly Gly Lys Gln Ser Lys Arg Pro Thr Gly Ser Ile
                100                 105                 110
Val Ala Pro Val Ser Cys Leu Gly Ile Leu Ser Met Ile Gly Pro Ala
            115                 120                 125
Val Tyr Phe Lys Phe Ser Arg Leu Met Glu Gly Gly Asp Ile Pro Val
    130                 135                 140
Ala Glu Met Gly Ile Thr Phe Ala Thr Phe Val Ala Ala Val Gly
145                 150                 155                 160
Thr Glu Phe Leu Ser Ala Trp Val His Lys Glu Leu Trp His Glu Ser
                165                 170                 175
Leu Trp Tyr Ile His Lys Ser His Arg Ser Arg Lys Gly Arg Phe
                180                 185                 190
Glu Phe Asn Asp Val Phe Ala Ile Ile Asn Ala Leu Pro Ala Ile Ala
            195                 200                 205
Leu Ile Asn Tyr Gly Phe Ser Asn Glu Gly Leu Leu Pro Gly Ala Cys
    210                 215                 220
Phe Gly Val Gly Leu Gly Thr Thr Val Cys Gly Met Ala Tyr Ile Phe
225                 230                 235                 240
Leu His Asn Gly Leu Ser His Arg Arg Phe Pro Val Trp Leu Ile Ala
                245                 250                 255
Asn Val Pro Tyr Phe His Lys Leu Ala Ala Ala His Gln Ile His His
                260                 265                 270
Ser Gly Lys Phe Gln Gly Val Pro Phe Gly Leu Phe Leu Gly Pro Lys
            275                 280                 285
Glu Leu Glu Glu Val Arg Gly Gly Thr Glu Glu Leu Glu Arg Val Ile
    290                 295                 300
Ser Arg Thr Thr Lys Arg Thr Gln Pro Ser Thr
305                 310                 315

<210> SEQ ID NO 9
<211> LENGTH: 1149
<212> TYPE: DNA
<213> ORGANISM: Adonis aestivalis

<400> SEQUENCE: 9
agcaatctca gtgttcagta caagttattc tttccacaag aatctcttgt tgcactcaaa     60
acaagacatt ctcaaccgcc catgtttgct cttctctcca gttgtggtgg agtcgcctat    120
gagaaagaaa aagacacatc gtgctgcatg tatctgctct gttgcagaga gaacaaggaa    180
ccttgatatt cctcaaattg aagaaggaga agagaacgag gaagaactaa tagaacagac    240
ggattctggc ataattcata taagaaaaac gctaggggga aaacaatcaa gacggtccac    300
tggctccatt gtcgcacccg tatcttgtct tgggatcctt tcaatgatcg gacctgctgt    360
ttacttcaag ttttcacggc taatggagtg tggagatatt cctgtcgcag aaatggggat    420
tacgtttgcc gcctttgttg ctgctgcgat tggcacggaa ttttgtcag gatgggttca    480
```

```
caaagaactc tggcacgatt ctttgtggta cattcacaag tctcaccata ggtcacgaaa    540
aggccgcttc gagttcaatg atgtgtttgc tattattaac gcgcttcctg ctattgctct    600
tatcaattat ggattctcaa atgaaggcct ccttcctgga gcctgctttg gtaccggtct    660
tggaacgaca gtctgtggca tggcttacat ttttcttcac aatggccttt cacaccgaag    720
gttcccagta gggcttattg caaacgtccc ttatttccac aagctggctg cagctcacca    780
aatccatcac tcaggaaaat tcagggtgt accatttggc ctgttccttg accccagga     840 attggaagaa gtaagaggag gcactgaaga attggagagg gtgatcagtc gtacagctaa    900
acgaacgcaa tcatctacat gaatcaactc ttttacattt atgaggtttt agtttatcgg    960
tgttacaagt cacacatttg tgtcgttgta gtaattcaaa gttaccatac tctttttag    1020 aatttttttt tgatgtatag gtcgcggagt tacggttaca aaggccaaat ctattgttgt    1080
ggaattccat tattaaaaat aaaaattaga gtttgtagtt ttatctggtg atcaatatca    1140
atatatatt                                                            1149

<210> SEQ ID NO 10
<211> LENGTH: 310
<212> TYPE: PRT
<213> ORGANISM: Arabidopsis
<220> FEATURE:
<221> NAME/KEY: misc_feature
<222> LOCATION: (4)..(4)
<223> OTHER INFORMATION: "Xaa" is any amino acid

<400> SEQUENCE: 10

Met Ala Ala Xaa Leu Ser Thr Ala Val Thr Phe Lys Pro Leu His Arg
1               5                   10                  15

Ser Phe Ser Ser Ser Thr Asp Phe Arg Leu Arg Leu Pro Lys Ser
            20                  25                  30

Leu Ser Gly Phe Ser Pro Ser Leu Arg Phe Lys Arg Phe Ser Val Cys
        35                  40                  45

Tyr Val Val Glu Glu Arg Arg Gln Asn Ser Pro Ile Glu Asn Asp Glu
    50                  55                  60

Arg Pro Glu Ser Thr Ser Ser Thr Asn Ala Ile Asp Ala Glu Tyr Leu
65                  70                  75                  80

Ala Leu Arg Leu Ala Glu Lys Leu Glu Arg Lys Ser Glu Arg Ser
                85                  90                  95

Thr Tyr Leu Ile Ala Ala Met Leu Ser Ser Phe Gly Ile Thr Ser Met
            100                 105                 110

Ala Val Met Ala Val Tyr Tyr Arg Phe Ser Trp Gln Met Glu Gly Gly
        115                 120                 125

Glu Ile Ser Met Leu Glu Met Phe Gly Thr Phe Ala Leu Ser Val Gly
    130                 135                 140

Ala Ala Val Gly Met Glu Phe Trp Ala Arg Trp Ala His Arg Ala Leu
145                 150                 155                 160

Trp His Ala Ser Leu Trp Asn Met His Glu Ser His His Lys Pro Arg
                165                 170                 175

Glu Gly Pro Phe Glu Leu Asn Asp Val Phe Ala Ile Val Asn Ala Gly
            180                 185                 190

Pro Ala Ile Gly Leu Leu Ser Tyr Gly Phe Phe Asn Lys Gly Leu Val
        195                 200                 205

Pro Gly Leu Cys Phe Gly Ala Gly Leu Gly Ile Thr Val Phe Gly Ile
    210                 215                 220
```

```
Ala Tyr Met Phe Val His Asp Gly Leu Val His Lys Arg Phe Pro Val
225                 230                 235                 240

Gly Pro Ile Ala Asp Val Pro Tyr Leu Arg Lys Val Ala Ala His
            245                 250                 255

Gln Leu His His Thr Asp Lys Phe Asn Gly Val Pro Tyr Gly Leu Phe
            260                 265                 270

Leu Gly Pro Lys Glu Leu Glu Glu Val Gly Gly Asn Glu Glu Leu Asp
            275                 280                 285

Lys Glu Ile Ser Arg Arg Ile Lys Ser Tyr Lys Lys Ala Ser Gly Ser
            290                 295                 300

Gly Ser Ser Ser Ser Ser
305                 310

<210> SEQ ID NO 11
<211> LENGTH: 60
<212> TYPE: DNA
<213> ORGANISM: Adonis aestivalis

<400> SEQUENCE: 11
cataccataa atagtagagg acaacctaca aaccaaccac cagaaacctc caatggcagc    60

<210> SEQ ID NO 12
<211> LENGTH: 309
<212> TYPE: PRT
<213> ORGANISM: Adonis aestivalis

<400> SEQUENCE: 12

Met Ala Ala Ala Ile Ser Val Phe Ser Ser Gly Tyr Ser Phe Tyr Lys
1               5                   10                  15

Asn Leu Leu Leu Asp Ser Lys Pro Asn Ile Leu Lys Pro Pro Cys Leu
                20                  25                  30

Leu Phe Ser Pro Val Val Ile Met Ser Pro Met Arg Lys Lys Lys Lys
            35                  40                  45

His Gly Asp Pro Cys Ile Cys Ser Val Ala Gly Arg Thr Arg Asn Leu
        50                  55                  60

Asp Ile Pro Gln Ile Glu Glu Glu Glu Asn Val Glu Glu Leu Ile
65                  70                  75                  80

Glu Gln Thr Asp Ser Asp Ile Val His Ile Lys Lys Thr Leu Gly Gly
                85                  90                  95

Lys Gln Ser Lys Arg Pro Thr Gly Ser Ile Val Ala Pro Val Ser Cys
            100                 105                 110

Leu Gly Ile Leu Ser Met Ile Gly Pro Ala Val Tyr Phe Lys Phe Ser
        115                 120                 125

Arg Leu Met Glu Gly Gly Asp Ile Pro Val Ala Glu Met Gly Ile Thr
130                 135                 140

Phe Ala Thr Phe Val Ala Ala Val Gly Thr Glu Phe Leu Ser Ala
145                 150                 155                 160

Trp Val His Lys Glu Leu Trp His Glu Ser Leu Trp Tyr Ile His Lys
                165                 170                 175

Ser His His Arg Ser Arg Lys Gly Arg Phe Glu Phe Asn Asp Val Phe
            180                 185                 190

Ala Ile Ile Asn Ala Leu Pro Ala Ile Ala Leu Ile Asn Tyr Gly Phe
        195                 200                 205

Ser Asn Glu Gly Leu Leu Pro Gly Ala Cys Phe Gly Val Gly Leu Gly
    210                 215                 220

Thr Thr Val Cys Gly Met Ala Tyr Ile Phe Leu His Asn Gly Leu Ser
```

```
                225                 230                 235                 240

His Arg Arg Phe Pro Val Trp Leu Ile Ala Asn Val Pro Tyr Phe His
                    245                 250                 255

Lys Leu Ala Ala Ala His Gln Ile His His Ser Gly Lys Phe Gln Gly
                260                 265                 270

Val Pro Phe Gly Leu Phe Leu Gly Pro Lys Glu Leu Glu Glu Val Arg
            275                 280                 285

Gly Gly Thr Glu Glu Leu Glu Arg Val Ile Ser Arg Thr Thr Lys Arg
        290                 295                 300

Thr Gln Pro Ser Thr
305

<210> SEQ ID NO 13
<211> LENGTH: 310
<212> TYPE: PRT
<213> ORGANISM: Arabidopsis
<220> FEATURE:
<221> NAME/KEY: misc_feature
<222> LOCATION: (4)..(4)
<223> OTHER INFORMATION: "Xaa" is any amino acid

<400> SEQUENCE: 13

Met Ala Ala Xaa Leu Ser Thr Ala Val Thr Phe Lys Pro Leu His Arg
1               5                   10                  15

Ser Phe Ser Ser Ser Thr Asp Phe Arg Leu Arg Leu Pro Lys Ser
                20                  25                  30

Leu Ser Gly Phe Ser Pro Ser Leu Arg Phe Lys Arg Phe Ser Val Cys
            35                  40                  45

Tyr Val Val Glu Glu Arg Arg Gln Asn Ser Pro Ile Glu Asn Asp Glu
    50                  55                  60

Arg Pro Glu Ser Thr Ser Ser Thr Asn Ala Ile Asp Ala Glu Tyr Leu
65                  70                  75                  80

Ala Leu Arg Leu Ala Glu Lys Leu Glu Arg Lys Lys Ser Glu Arg Ser
                85                  90                  95

Thr Tyr Leu Ile Ala Ala Met Leu Ser Ser Phe Gly Ile Thr Ser Met
            100                 105                 110

Ala Val Met Ala Val Tyr Tyr Arg Phe Ser Trp Gln Met Glu Gly Gly
        115                 120                 125

Glu Ile Ser Met Leu Glu Met Phe Gly Thr Phe Ala Leu Ser Val Gly
    130                 135                 140

Ala Ala Val Gly Met Glu Phe Trp Ala Arg Trp Ala His Arg Ala Leu
145                 150                 155                 160

Trp His Ala Ser Leu Trp Asn Met His Glu Ser His His Lys Pro Arg
                165                 170                 175

Glu Gly Pro Phe Glu Leu Asn Asp Val Phe Ala Ile Val Asn Ala Gly
            180                 185                 190

Pro Ala Ile Gly Leu Leu Ser Tyr Gly Phe Phe Asn Lys Gly Leu Val
        195                 200                 205

Pro Gly Leu Cys Phe Gly Ala Gly Leu Gly Ile Thr Val Phe Gly Ile
    210                 215                 220

Ala Tyr Met Phe Val His Asp Gly Leu Val His Lys Arg Phe Pro Val
225                 230                 235                 240

Gly Pro Ile Ala Asp Val Pro Tyr Leu Arg Lys Val Ala Ala Ala His
                245                 250                 255

Gln Leu His His Thr Asp Lys Phe Asn Gly Val Pro Tyr Gly Leu Phe
            260                 265                 270
```

```
Leu Gly Pro Lys Glu Leu Glu Val Gly Gly Asn Glu Glu Leu Asp
        275                 280                 285
Lys Glu Ile Ser Arg Arg Ile Lys Ser Tyr Lys Lys Ala Ser Gly Ser
    290                 295                 300
Gly Ser Ser Ser Ser
305             310

<210> SEQ ID NO 14
<211> LENGTH: 305
<212> TYPE: PRT
<213> ORGANISM: Arabidopsis

<400> SEQUENCE: 14

Met Ala Ala Gly Leu Ser Thr Ile Ala Val Thr Leu Lys Pro Leu Asn
1               5                   10                  15
Arg Ser Ser Phe Ser Ala Asn His Pro Ile Ser Thr Ala Val Phe Pro
            20                  25                  30
Pro Ser Leu Arg Phe Asn Gly Phe Arg Arg Arg Lys Ile Leu Thr Val
            35                  40                  45
Cys Phe Val Val Glu Glu Arg Lys Gln Ser Ser Pro Met Asp Asp Asp
    50                  55                  60
Asn Lys Pro Glu Ser Thr Thr Ser Ser Ser Glu Ile Leu Met Thr Ser
65                  70                  75                  80
Arg Leu Leu Lys Lys Ala Glu Lys Lys Lys Ser Glu Arg Phe Thr Tyr
                85                  90                  95
Leu Ile Ala Ala Val Met Ser Ser Phe Gly Ile Thr Ser Met Ala Ile
            100                 105                 110
Met Ala Val Tyr Tyr Arg Phe Ser Trp Gln Met Lys Gly Gly Glu Val
            115                 120                 125
Ser Val Leu Glu Met Phe Gly Thr Phe Ala Leu Ser Val Gly Ala Ala
        130                 135                 140
Val Val Gly Met Glu Phe Trp Ala Arg Trp Ala His Arg Ala Leu Trp
145                 150                 155                 160
His Asp Ser Leu Trp Asn Met His Glu Ser His His Lys Pro Arg Glu
                165                 170                 175
Gly Ala Phe Glu Leu Asn Asp Val Phe Ala Ile Thr Asn Ala Val Pro
            180                 185                 190
Ala Ile Gly Leu Leu Tyr Tyr Gly Phe Leu Asn Lys Gly Leu Val Pro
            195                 200                 205
Gly Leu Cys Phe Gly Ala Gly Leu Gly Ile Thr Met Phe Gly Met Ala
        210                 215                 220
Tyr Met Phe Val His Asp Gly Leu Val His Lys Arg Phe Pro Val Gly
225                 230                 235                 240
Pro Ile Ala Asn Val Pro Tyr Leu Arg Lys Val Ala Ala His Gln
            245                 250                 255
Leu His His Thr Asp Lys Phe Lys Gly Val Pro Tyr Gly Leu Phe Leu
                260                 265                 270
Gly Pro Lys Gln Glu Val Glu Val Gly Gly Lys Glu Glu Leu Glu
        275                 280                 285
Lys Glu Ile Ser Arg Arg Ile Lys Leu Tyr Asn Lys Gly Ser Ser Thr
    290                 295                 300
Ser
305
```

```
<210> SEQ ID NO 15
<211> LENGTH: 315
<212> TYPE: PRT
<213> ORGANISM: Capsicum annuum

<400> SEQUENCE: 15

Met Ala Ala Glu Ile Ser Ile Ser Ala Ser Ser Arg Ala Ile Cys Leu
1               5                   10                  15

Gln Arg Asn Pro Phe Pro Ala Pro Lys Tyr Phe Ala Thr Ala Pro Pro
            20                  25                  30

Leu Leu Phe Phe Ser Pro Leu Thr Cys Asn Leu Asp Ala Ile Leu Arg
        35                  40                  45

Ser Arg Arg Lys Pro Arg Leu Ala Ala Cys Phe Val Leu Lys Asp Asp
    50                  55                  60

Lys Leu Tyr Thr Ala Gln Ser Gly Lys Gln Ser Asp Thr Glu Ala Ile
65                  70                  75                  80

Gly Asp Glu Ile Glu Val Glu Thr Asn Glu Gly Lys Ser Leu Ala Val
                85                  90                  95

Arg Leu Ala Glu Lys Phe Ala Arg Lys Lys Ser Glu Arg Phe Thr Tyr
            100                 105                 110

Leu Val Ala Ala Val Met Ser Ser Leu Gly Ile Thr Ser Met Ala Val
        115                 120                 125

Ile Ser Val Tyr Arg Phe Ser Trp Gln Met Glu Gly Gly Glu Met
130                 135                 140

Pro Phe Ser Glu Met Phe Cys Thr Phe Ala Leu Ala Phe Gly Ala Ala
145                 150                 155                 160

Ile Gly Met Glu Tyr Trp Ala Arg Trp Ala His Arg Ala Leu Trp His
            165                 170                 175

Ala Ser Leu Trp His Met His Glu Ser His His Arg Pro Arg Glu Gly
        180                 185                 190

Pro Phe Glu Leu Asn Asp Ile Phe Ala Ile Ile Asn Ala Val Pro Ala
    195                 200                 205

Ile Ala Phe Phe Ser Phe Gly Phe Asn His Lys Gly Leu Ile Pro Gly
        210                 215                 220

Ile Cys Phe Gly Ala Gly Leu Gly Ile Thr Val Phe Gly Met Ala Tyr
225                 230                 235                 240

Met Phe Val His Asp Gly Leu Val His Lys Arg Phe Pro Val Gly Pro
                245                 250                 255

Ile Ala Lys Val Pro Tyr Phe Gln Arg Val Ala Ala Ala His Gln Leu
            260                 265                 270

His His Ser Asp Lys Phe Asp Gly Val Pro Tyr Gly Leu Phe Leu Gly
        275                 280                 285

Pro Lys Glu Leu Glu Glu Val Gly Val Ile Glu Glu Leu Glu Lys Glu
    290                 295                 300

Val Asn Arg Arg Ile Lys Ser Leu Lys Arg Leu
305                 310                 315

<210> SEQ ID NO 16
<211> LENGTH: 316
<212> TYPE: PRT
<213> ORGANISM: Capsicum annuum

<400> SEQUENCE: 16

Thr Thr Gly Arg Tyr His Tyr Gln Leu Val Trp Cys Gln Ile Ser Phe
1               5                   10                  15

Ser Ser Thr Ser Arg Thr Ser Tyr Tyr Arg His Ser Pro Phe Leu Gly
```

```
            20                  25                  30
Pro Lys Pro Thr Pro Thr Thr Pro Ser Val Tyr Pro Ile Thr Pro Phe
    35                  40                  45

Ser Pro Asn Leu Gly Ser Ile Leu Arg Cys Arg Arg Arg Pro Ser Phe
50                  55                  60

Thr Val Cys Phe Val Leu Glu Asp Asp Lys Phe Lys Thr Gln Phe Glu
65                  70                  75                  80

Ala Gly Glu Glu Asp Ile Glu Met Lys Ile Glu Glu Gln Ile Ser Ala
                85                  90                  95

Thr Arg Leu Ala Glu Lys Leu Ala Arg Lys Ser Glu Arg Phe Thr
            100                 105                 110

Tyr Leu Val Ala Ala Val Met Ser Ser Phe Gly Ile Thr Ser Met Ala
            115                 120                 125

Val Met Ala Val Tyr Tyr Arg Phe Tyr Trp Gln Met Glu Gly Gly Glu
130                 135                 140

Val Pro Phe Ser Glu Met Phe Gly Thr Phe Ala Leu Ser Val Gly Ala
145                 150                 155                 160

Ala Val Gly Met Glu Phe Trp Ala Arg Trp Ala His Lys Ala Leu Trp
                165                 170                 175

His Ala Ser Leu Trp His Met His Glu Ser His His Lys Pro Arg Glu
                180                 185                 190

Gly Pro Phe Glu Leu Asn Asp Val Phe Ala Ile Ile Asn Ala Val Pro
            195                 200                 205

Ala Ile Ala Leu Leu Asp Tyr Gly Phe Phe His Lys Gly Leu Ile Pro
210                 215                 220

Gly Leu Cys Phe Gly Ala Gly Leu Gly Ile Thr Val Phe Gly Met Ala
225                 230                 235                 240

Tyr Met Phe Val His Asp Gly Leu Val His Lys Arg Phe Pro Val Gly
                245                 250                 255

Pro Val Ala Asn Val Pro Tyr Leu Arg Lys Val Ala Ala His Ser
                260                 265                 270

Leu His His Ser Glu Lys Phe Asn Gly Val Pro Tyr Gly Leu Phe Leu
            275                 280                 285

Gly Pro Lys Glu Leu Glu Glu Val Gly Gly Leu Glu Glu Leu Glu Lys
            290                 295                 300

Glu Val Asn Arg Arg Thr Arg Tyr Ile Lys Gly Ser
305                 310                 315
```

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 17
cagaatcggt ctgttctatt agttcttcc                                    29

<210> SEQ ID NO 18
<211> LENGTH: 32
<212> TYPE: DNA
<213> ORGANISM: Artificial Sequence
<220> FEATURE:

-continued

<223> OTHER INFORMATION: Description of Artificial Sequence: Synthetic

<400> SEQUENCE: 18
caatttgagg aatatcaagg ttccttgttc tc                              32

US 6,551,807 B1

CAROTENOID KETOLASE GENES AND GENE PRODUCTS, PRODUCTION OF KETOCAROTENOIDS AND METHODS OF MODIFYING CAROTENOIDS USING THE GENES

This application is a 371 of PCT//US99/10455 filed May. 21, 1999, which claims the benefit of U.S. provisional application No. 60/086,460, filed May 22, 1998.

BACKGROUND OF THE INVENTION

Carotenoids are widely distributed natural pigments that are responsible for many of the yellow, orange and red colors seen in living organisms. They have important commercial uses as coloring agents in the food industry, as feed and food additives, in cosmetics and as provitamin A precursors.

The plant species *Adonis aestivalis* produces flowers with petals that are deep red in color and nearly black at the base of the petals due to the accumulation of ketocarotenoid and other carotenoid pigments (Neamtu et al., *Rev. Roum. Biochim.* 6:157, 1969). This pattern of carotenoid accumulation accounts for the common name of some varieties of this species: summer pheasant's eye.

Among the carotenoids identified in the petals of the red petal varieties of these various species is the ketocarotenoid astaxanthin (3,3'-dihydroxy-4,4'-diketo-b,b-carotene; see FIG. 1). Various other ketocarotenoids (see FIG. 1) including 3-hydroxyechinenone (3-hydroxy-4-keto-b,b-carotene), adonirubin (3-hydroxy-4,4'-diketo-b,b-carotene) adonixanthin (3,3'-dihydroxy-4-keto-b,b-carotene) and isozeaxanthin (4,4'-dihydroxy-b,b-carotene; see T. W. Goodwin, The Biochemistry of the Carotenoids, vol I. Plants, 2nd edition, 1980, page 147) have also been reported. The latter compound is consistent with speculation that the 4-hydroxy may be an intermediate in the formation of the 4-keto group.

SUMMARY OF THE INVENTION

There is appreciable interest in the biological production of carotenoids, in particular the orange-colored ketocarotenoids such as astaxanthin and canthaxanthin (FIG. 1), and in the modification of carotenoid composition. For this reason, an *A. aestivalis* flower cDNA library was constructed and screened for cDNAs encoding enzymes (hereinafter referred to as "ketolases" although the specific biochemical activity has not yet been established) involved in the conversion of b-carotene into orange compounds with absorption properties similar to those exhibited by common ketocarotenoids such as canthaxanthin (FIG. 1). Two distinctly different *Adonis aestivalis* cDNAs were obtained from among a number of cDNAs that were selected on this basis.

Thus, a first aspect of the present invention is a purified nucleic acid sequence which encodes for a protein having ketolase enzyme activity and has the nucleic acid sequence of SEQ ID NO: 1 or 3.

The invention also includes a purified nucleic acid sequence which encodes for a protein having ketolase enzyme activity and having the amino acid sequence of SEQ ID NO: 2 or 4.

The invention also includes vectors which comprise any portion of the nucleic acid sequences listed above, and host cells transformed with such vectors.

Another aspect of the present invention is a method of producing a ketocarotenoid in a host cell, the method comprising inserting into the host cell a vector comprising a heterologous nucleic acid sequence which encodes for a protein having ketolase enzyme activity and comprises (1) SEQ ID NO: 1 or 3 or (2) a sequence which encodes the amino acid sequence of SEQ ID NO: 2 or 4, wherein the heterologous nucleic acid sequence is operably linked to a promoter; and expressing the heterologous nucleic acid sequence, thereby producing the ketolase enzyme.

Another subject of the present invention is a method of modifying the production of carotenoids in a host cell, relative to an untransformed host cell, the method comprising inserting into a host cell which already produces carotenoids a vector comprising a heterologous nucleic acid sequence which encodes for a protein having ketolase enzyme activity and comprises (1) SEQ ID NO: 1 or 3 or (2) a sequence which encodes the amino acid sequence of SEQ ID NO: 2 or 4, wherein the heterologous nucleic acid sequence is operably linked to a promoter; and expressing the heterologous nucleic acid sequence in the host cell to modify the production of the carotenoids in the host cell, relative to an untransformed host cell.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 2 illustrates the beta ring structure of b-carotene and various modifications of this parent ring that might be produced through the action of the products of the *A. aestivalis* ketolase cDNAs. Also shown is the structure of the epsilon ring, not found to be a substrate for the *A. aestivalis* ketolases and present in carotenoids such as d-carotene, e-carotene, a-carotene and lutein.

FIG. 5 shows SEQ ID NO: 5 (the sequence shown in this Figure includes SEQ ID NO: 1 and also includes some of the flanking DNA from the adaptor DNA and the multiple cloning site (MCS) of the library cloning vector, which sequences are shown in bold).

FIG. 6 shows SEQ ID NO: 6 (the sequence shown in this Figure includes SEQ ID NO: 2 and also includes a translation of amino acids resulting from the adaptor DNA and the multiple cloning site (MCS) of the library cloning vector and the start codon from the plasmid vector pTrcHis, which sequences are shown in bold and capitalized).

FIG. 7 shows SEQ ID NO: 7 (the sequence shown in this Figure includes SEQ ID NO: 3 and also includes some of the flanking DNA from the adaptor DNA and the multiple cloning site (MCS) of the library cloning vector, which sequences are shown in bold).

FIG. 8 shows SEQ ID NO: 8 (the sequence shown in this Figure includes SEQ ID NO: 4 and also includes a translation of amino acids resulting from the adaptor DNA and the multiple cloning site (MCS) of the library cloning vector and the start codon from the plasmid vector, which sequences are shown in bold and capitalized).

FIG. 9 shows a "Gap" alignment of the two Adonis ketolase sequences of the invention. A truncated version of SEQ ID NO: 1 is shown in this Figure for comparitive purposes, and is designated SEQ ID NO: 9. The percentage identity was calculated to be 91.107.

FIG. 10 shows a "Gap" alignment of SEQ ID NO: 2 and 4. The following results were found:

Figure 1:
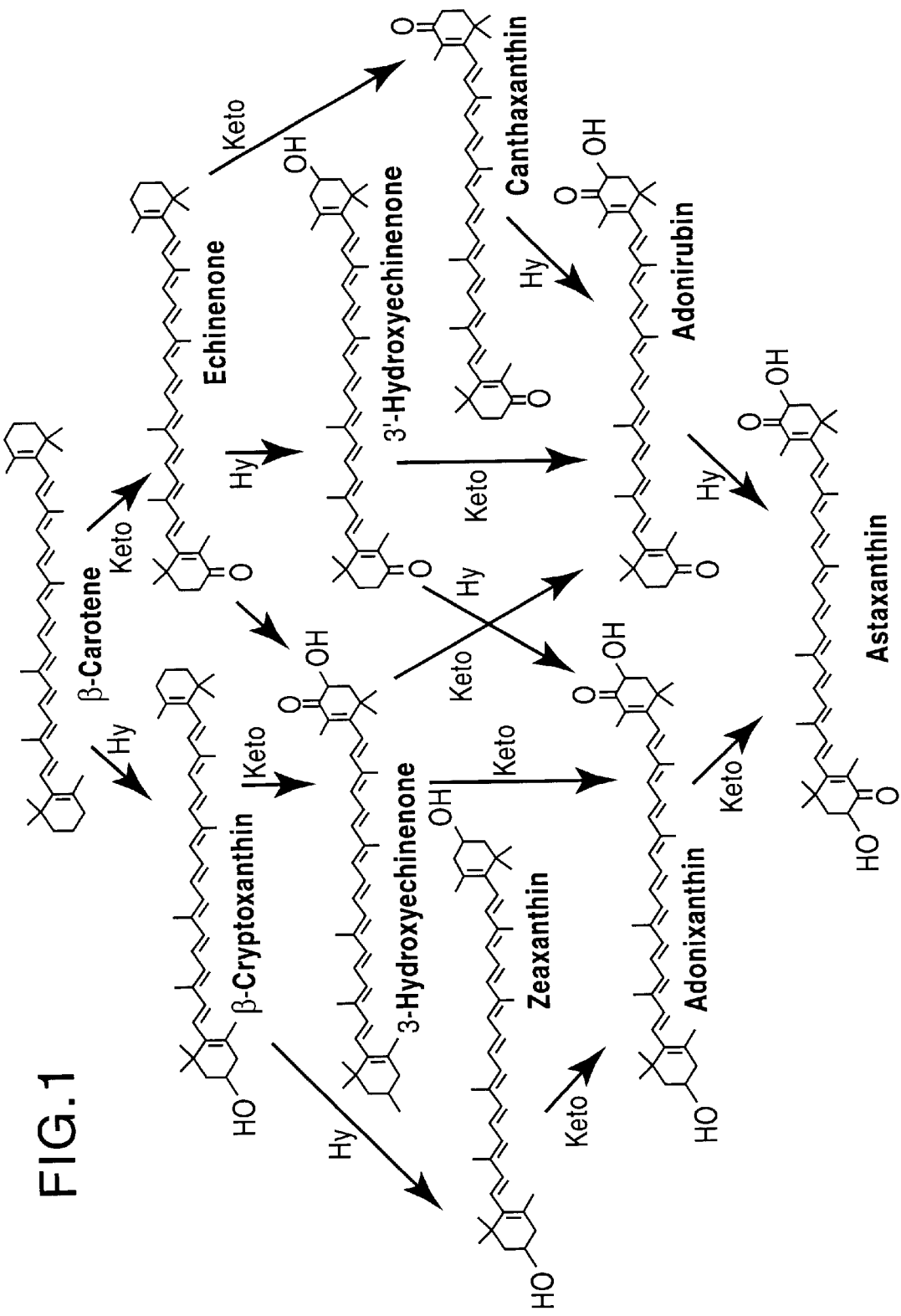
FIG. 1 illustrates structures and biochemical routes leading from b-carotene to various of the ketocarotenoids referred to in the text. Conversion of β-carotene to astaxanthin by a hydroxylase enzyme (Hy) and a ketolase enzyme (keto) could proceed via any one or all of several possible routes depending on the order of the reactions.

| Gap weight: | 12 | average match: | 2.912 |
| Length weight: | 4 | average mismatch: | −2.003 |
| Quality: | 1440 | length: | 307 |
| Ratio: | 4.691 | gaps: | 0 |
| percent similarity: | 92.182 | percent identity: | 90.228 |

FIG. 11 shows a comparison between SEQ ID NO: 2 and the *Arabidopsis thaliana* β-carotene hydroxylase enzyme (GenBank U58919) (SEQ ID NO: 10).

FIG. 12A shows gDNA (SEQ ID NO: 11) immediately upstream of the cDNA of SEQ ID NO: 3. The sequence was obtained from a PCR product generated using the GenomeWalker kit of Clontech Laboratories, Inc. (1020 East Meadow Circle, Palo Alto, Calif. 94303-4230) and nested primers specific to the ketolases of *Adonis aestivalis* (cagaatcggtctgttctattagttcttcc (SEQ ID NO: 17) and caatttgaggaatatcaaggttccttgttctc (SEQ ID NO: 18)). The termination codon upstream of and in-frame with initiation codon (TAA at positions 204–206) is shown in bold. Initiation codon (ATG) is also shown in bold.

FIG. 12B (SEQ ID NO: 12) indicates that the full length polypeptide of SEQ ID NO: 4 begins with the amino acids MAA (shown in bold) immediately preceding the ketolase sequence shown in FIG. 8. A similar MAA amino acid sequence immediately preceding SEQ ID NO: 1 is also expected.

FIG. 13 shows an alignment of SEQ ID NO: 2, SEQ ID NO: 12, an Arabidopsis β-carotene hydroxylase enzyme (predicted product of GenBank U58919) (SEQ ID NO: 13), a putative second Arabidopsis hydroxylase predicted by genomic DNA sequence (GenBank AB025606; the exon/intron junctions were chosen with reference to the product of the Arabidopsis β-carotene hydroxylase cDNA u58919) (SEQ ID NO: 14), and two *Capsicum annuum* β-carotene hydroxylases (predicted products of GenBank Y09722 and Y09225) (SEQ ID NO: 15 and 16).

DESCRIPTION OF THE PREFERRED EMBODIMENTS

The present invention is directed to a purified nucleic acid sequence which encodes for a protein having ketolase enzyme activity and has the nucleic acid sequence of SEQ ID NO: 1 or 3.

The invention also includes a purified nucleic acid sequence which encodes for a protein having ketolase enzyme activity and having the amino acid sequence of SEQ ID NO: 2 or 4.

Two different but closely-related nucleic acids have been isolated. The sequences of the longest example of each are presented herein. Sequencing which has subsequently been conducted of upstream genomic DNA indicates that SEQ ID NO: 3 lacks bases encoding the first three amino acids (MAA; see FIG. 12). Likely, this is also the case for SEQ ID NO: 1, but the upstream genomic sequences have not yet been obtained for this nucleic acid.

The two different Adonis ketolases denoted in SEQ ID NO: 1 and 3 are similar in sequence, sharing about 91% identity, as determined by the Gap program discussed below (see FIG. 9). The predicted amino acid sequences of the enzymes denoted in SEQ ID NO: 2 and 4 share about 92% similarity and about 90% identity, also as determined by the Gap program (see FIG. 10).

Therefore, it is clear that certain modifications of SEQ ID NO: 1 or 3 or SEQ ID NO: 2 or 4 can take place without destroying the activity of the enzyme. Note also that certain truncated versions of the cDNAs of SEQ ID NO: 1 or 3 were found to be functional (i.e., these cDNAs retained the property of causing the conversion of b-carotene to orange compounds). Also, the Arabidopsis β-carotene hydroxylase (GenBank U58919), aligned with the ketolase SEQ ID NO: 2 in FIG. 11, retains catalytic function when truncated to yield a polypeptide that lacks the first 129 amino acids (Sun et al., 1996). From the alignment in FIG. 11, therefore, this would suggest that the two ketolases of the invention retain catalytic activity after truncation to remove bases encoding the first 132 amino acids.

Thus, the present invention is intended to include those ketolase nucleic acid and amino acid sequences in which substitutions, deletions, additions or other modifications have taken place, as compared to SEQ ID NO: 1 or 3 or SEQ ID NO: 2 or 4, without destroying the activity of the ketolase enzyme. Preferably, the substitutions, deletions, additions or other modifications take place at those positions which already show dissimilarity between the present sequences. For SEQ ID NO: 1, as shown in FIG. 9, these positions are as follows: positions 7, 20, 23, 35, 53, 63, 65, 67, 76, 78, 85, 86, 91, 107, 109–111, 135, 140, 144, 146, 160, 168, 217, 219, 241, 249, 254, 256, 271, 291, 296, 349, 389, 400, 406, 431, 448, 449, 460, 471, 499, 530, 589, 619, 643, 653, 654, 667, 679, 709, 731, 742, 784, 787, 836, 871, 883, 896, 911, 919, 928, 930, 939, 943, 967, 969, 978, 979, 982, 988, 995, 1005, 1006, 1012–1014, 1017, 1019–1021, 1023, 1025, 1049, 1050, 1054, 1060–1068, 1070–1073, 1075, 1094, 1100, 1101, 1106, 1107, 1109 and 1111–1176. For SEQ ID NO: 3, as shown in FIG. 9, these positions are as follows: positions 7, 20, 23, 35, 53, 63, 65, 67, 76, 78, 85, 86, 91, 107, 109–111, 135, 140, 144, 146, 160, 168, 217, 219, 241, 249, 254, 256, 271, 291, 296, 349, 389, 400, 406, 431, 448, 449, 460, 471, 499, 530, 589, 619, 643, 653, 654, 667, 679, 709, 731, 742, 784, 787, 836, 871, 883, 896, 911, 919, 928, 930, 939, 943, 966, 967, 970, 979, 980, 983, 989, 996, 1006, 1007, 1013–1015, 1018, 1020–1022, 1024, 1026, 1050, 1051, 1055, 1062–1065, 1067, 1086, 1092, 1093, 1098, 1099, 1101 and 1103–1112.

For SEQ ID NO: 2 and 4, as shown in FIG. 10, the following amino acids can be substituted or deleted, or additions or other modifications can be made, without destroying the activity of the ketolase enzyme: positions 7, 8, 12, 18, 21, 22, 25, 26, 36, 37, 45, 47–49, 56, 73, 83, 85, 97, 99, 130, 144, 150, 157, 166, 218, 244, 279, 299 and 304. Therefore, the present invention also intends to cover amino acid sequences where such changes have been made.

In each case, nucleic acid and amino acid sequence similarity and identity is measured using sequence analysis software, for example, the Sequence Analysis, Gap, or BestFit software packages of the Genetics Computer Group (University of Wis. Biotechnology Center, 1710 University Avenue, Madison, Wis. 53705), MEGAlign (DNAStar, Inc., 1228 S. Park St., Madison, Wis. 53715), or MacVector (Oxford Molecular Group, 2105 S. Bascom Avenue, Suite 200, Campbell, Calif. 95008). Such software uses algorithms to match similar sequences by assigning degrees of identity to various substitutions, deletions, and other modifications, and includes detailed instructions as to useful parameters, etc., such that those of routine skill in the art can easily compare sequence similarities and identities. An example of a useful algorithm in this regard is the algorithm of Needleman and Wunsch, which is used in the Gap program discussed above. This program finds the alignment of two complete sequences that maximizes the number of matches and minimizes the number of gaps. Another useful algorithm is the algorithm of Smith and Waterman, which is used in the BestFit program discussed above. This program creates an optimal alignment of the best segment of similarity between two sequences. Optimal alignments are found by inserting gaps to maximize the number of matches using the local homology algorithm of Smith and Waterman.

Conservative (i.e. similar) substitutions typically include substitutions within the following groups: glycine and alanine; valine, isoleucine and leucine; aspartic acid, glutamic acid, asparagine and glutamine; serine and threonine; lysine and arginine; and phenylalanine and tyrosine. Substitutions may also be made on the basis of conserved hydrophobicity or hydrophilicity (see Kyte and Doolittle, *J. Mol. Biol.* 157: 105–132 (1982)), or on the basis of the ability to assume similar polypeptide secondary structure (see Chou and Fasman, *Adv. Enzymol.* 47: 45–148 (1978)).

If comparison is made between nucleotide sequences, preferably the length of comparison sequences is at least 50 nucleotides, more preferably at least 60 nucleotides, at least 75 nucleotides or at least 100 nucleotides. It is most preferred if comparison is made between the nucleic acid sequences encoding the enzyme coding regions necessary for enzyme activity. If comparison is made between amino acid sequences, preferably the length of comparison is at least 20 amino acids, more preferably at least 30 amino acids, at least 40 amino acids or at least 50 amino acids. It is most preferred if comparison is made between the amino acid sequences in the enzyme coding regions necessary for enzyme activity.

While the two different Adonis ketolase enzymes of the present invention are similar in sequence, previously-described bacterial (Misawa et al., 1995), cyanobacterial (Fernandez-Gonzalez et al.,1997), and green algal (*Haematococcus pluvialis*; Lotan et al., 1995; Kajiwara et al., 1995) β-carotene ketolase enzymes bear little resemblance to the Adonis ketolases, although certain histidine motifs and features of the predicted secondary structure are common to the polypeptides predicted by both groups (Cunningham and Gantt, 1998).

The present invention also includes vectors containing the nucleic acids of the invention. Suitable vectors according to the present invention comprise a gene encoding a ketolase enzyme as described above, wherein the gene is operably linked to a suitable promoter. Suitable promoters for the vector can be constructed using techniques well known in the art (see, for example, Sambrook et al., *Molecular Cloning A Laboratory Manual*, Cold Spring Harbor Laboratory, Cold Spring Harbor, N.Y., 1989; Ausubel et al., *Current Protocols in Molecular Biology*, Greene Publishing and Wiley Interscience, New York, 1991). Suitable vectors for eukaryotic expression in plants are described in Fray et al., (1995; *Plant J*. 8:693–701) and Misawa et al, (1994; *Plant J*. 6:481–489). Suitable vectors for prokaryotic expression include pACYC184, pUC119, and pBR322 (available from New England BioLabs, Bevery, Mass.) and pTrcHis (Invitrogen) and pET28 (Novagen) and derivatives thereof. The vectors of the present invention can additionally contain regulatory elements such as promoters, repressors, selectable markers such as antibiotic resistance genes, etc., the construction of which is very well known in the art.

The genes encoding the ketolase enzymes as described above, when cloned into a suitable expression vector, can be used to overexpress these enzymes in a host cell expression system or to inhibit the expression of these enzymes. For example, a vector containing a gene of the invention may be used to increase the amount of ketocarotenoids in an organism and thereby alter the nutritional or commercial value or pharmacology of the organism. A vector containing a gene of the invention may also be used to modify the carotenoid production in an organism.

Therefore, the present invention includes a method of producing a ketocarotenoid in a host cell, the method comprising
  inserting into the host cell a vector comprising a heterologous nucleic acid sequence which encodes for a protein having ketolase enzyme activity and comprises (1) SEQ ID NO: 1 or 3 or (2) a sequence which encodes the amino acid sequence of SEQ ID NO: 2 or 4, wherein the heterologous nucleic acid sequence is operably linked to a promoter; and
  expressing the heterologous nucleic acid sequence, thereby producing the ketocarotenoid.

The present invention also includes a method of modifying the production of carotenoids in a host cell, relative to an untransformed host cell, the method comprising
  inserting into a host cell which already produces carotenoids a vector comprising a heterologous nucleic acid sequence which encodes for a protein having ketolase enzyme activity and comprises (1) SEQ ID NO: 1 or 3 or (2) a sequence which encodes the amino acid sequence of SEQ ID NO: 2 or 4, wherein the heterologous nucleic acid sequence is operably linked to a promoter; and
  expressing the heterologous nucleic acid sequence in the host cell to modify the production of the carotenoids in the host cell, relative to an untransformed host cell.

The term "modifying the production" means that the amount of carotenoids produced can be enhanced, reduced, or left the same, as compared to an untransformed host cell. In accordance with one embodiment of the present invention, the make-up of the carotenoids (i.e., the type of carotenoids produced) is changed vis a vis each other, and this change in make-up may result in either a net gain, net loss, or no net change in the amount of carotenoids produced in the cell. In accordance with another embodiment of the present invention, the production or the biochemical activity of the carotenoids (or the enzymes which catalyze their formation) is enhanced by the insertion of the ketolase enzyme-encoding nucleic acid. In yet another embodiment of the invention, the production or the biochemical activity of the carotenoids (or the enzymes which catalyze their formation) may be reduced or inhibited by a number of different approaches available to those skilled in the art, including but not limited to such methodologies or approaches as anti-sense (e.g., Gray et al. (1992), *Plant Mol. Biol.* 19:69–87), ribozymes (e.g., Wegener et al (1994) *Mol. Gen. Genet.* Nov. 15, 1994; 245(4):465–470), co-suppression (e.g. Fray et al. (1993) *Plant Mol. Biol.* 22:589–602), targeted disruption of the gene (e.g., Schaefer et al. *Plant J.* 11:1195–1206, 1997), intracellular antibodies (e.g., see Rondon et al. (1 997) *Annu. Rev. Microbiol.* 51:257–283) or whatever other approaches rely on the knowledge or availability of the nucleic acid sequences of the invention, or the enzymes encoded thereby.

Host systems according to the present invention preferably comprise any organism which is capable of producing carotenoids, or which already produces carotenoids. Such organisms include plants, algae, certain bacteria, cyanobacteria and other photosynthetic bacteria. Transformation of these hosts with vectors according to the present invention can be done using standard techniques. See, for example, Sambrook et al., *Molecular Cloning A Laboratory Manual*, Cold Spring Harbor Laboratory, Cold Spring Harbor, N.Y., 1989; Ausubel et al., *Current Protocols in Molecular Biology*, Greene Publishing and Wiley Interscience, New York, 1991.

Alternatively, transgenic organisms can be constructed which include the nucleic acid sequences of the present invention. The incorporation of these sequences can allow the controlling of carotenoid biosynthesis, content, or composition in the host cell. These transgenic systems can be constructed to incorporate sequences which allow for the overexpression of the various nucleic acid sequences of the present invention. Transgenic systems can also be constructed which allow for the underexpression of the various nucleic acid sequences of the present invention. Such systems may contain anti-sense expression of the nucleic acid sequences of the present invention. Such anti-sense expression would result in the accumulation of the substrates of the enzyme encoded by the sense strand.

Having generally described this invention, a further understanding can be obtained by reference to certain specific examples which are provided herein for purposes of illustration only and are not intended to be limiting unless otherwise specified.

EXAMPLE 1

Isolation of Plant cDNAs that Convert b-Carotene into Compounds with Ketocarotenoid-like Spectra A flower cDNA library from the plant *Adonis aestivalis* was introduced into a strain of *Escherichia coli* engineered to accumulate the yellow carotenoid pigment β-carotene (see Cunningham et al., *Plant Cell* 8:1613–26, 1996). This strain of *E. coli* normally forms yellow colonies when cultures are spread on a solid agar growth medium. Keto-carotenoids that are derived from b-carotene, such as echinenone and canthaxanthin (FIG. 1), are, in contrast, orange to orange-red in color. Colonies that were orange rather than yellow in color were visually selected, and the DNA sequences of the *Adonis aestivalis* cDNAs within the plasmid vectors contained in these colonies were ascertained. Two distinct cDNAs were obtained from analysis of cDNA inserts in plasmids obtained from approximately 10 selected colonies. The DNA sequences of these two ketolase cDNAs are presented herein.

Figure 3:
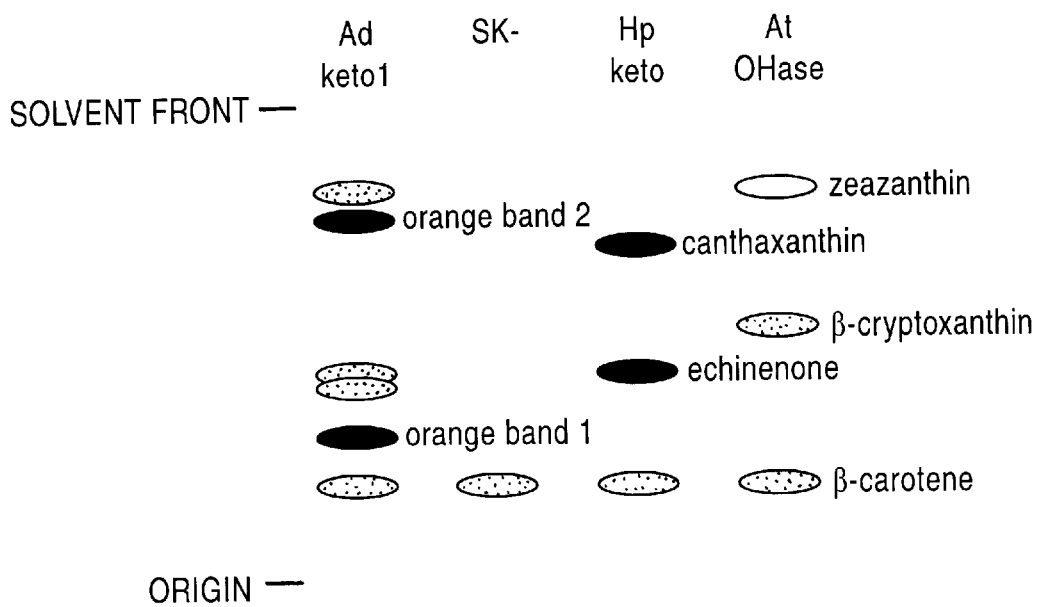
FIG. 3 illustrate results obtained with TLC (thin layer chromatography) separation of carotenoid pigments extracted from *E. coli* cultures, previously engineered to produce b-carotene, but that now also contain the *A. aestivalis* ketolase cDNAs and/or other introduced genes and cDNAs. The Figure indicates the empty plasmid vector pBluescript SK- (SK-), the *Adonis aestivalis* ketolase 1 cDNA in this plasmid vector (Ad keto1), the *Haematococcus pluvialis* ketolase cDNA in this plasmid vector Hp keto), or the Arabidopsis β-carotene hydroxylase cDNA (At Ohase). Bands that were orange in color are shown here with a darker fill than those with a yellow color. Identities of various bands are indicated to the right of the band.
Figure 4:
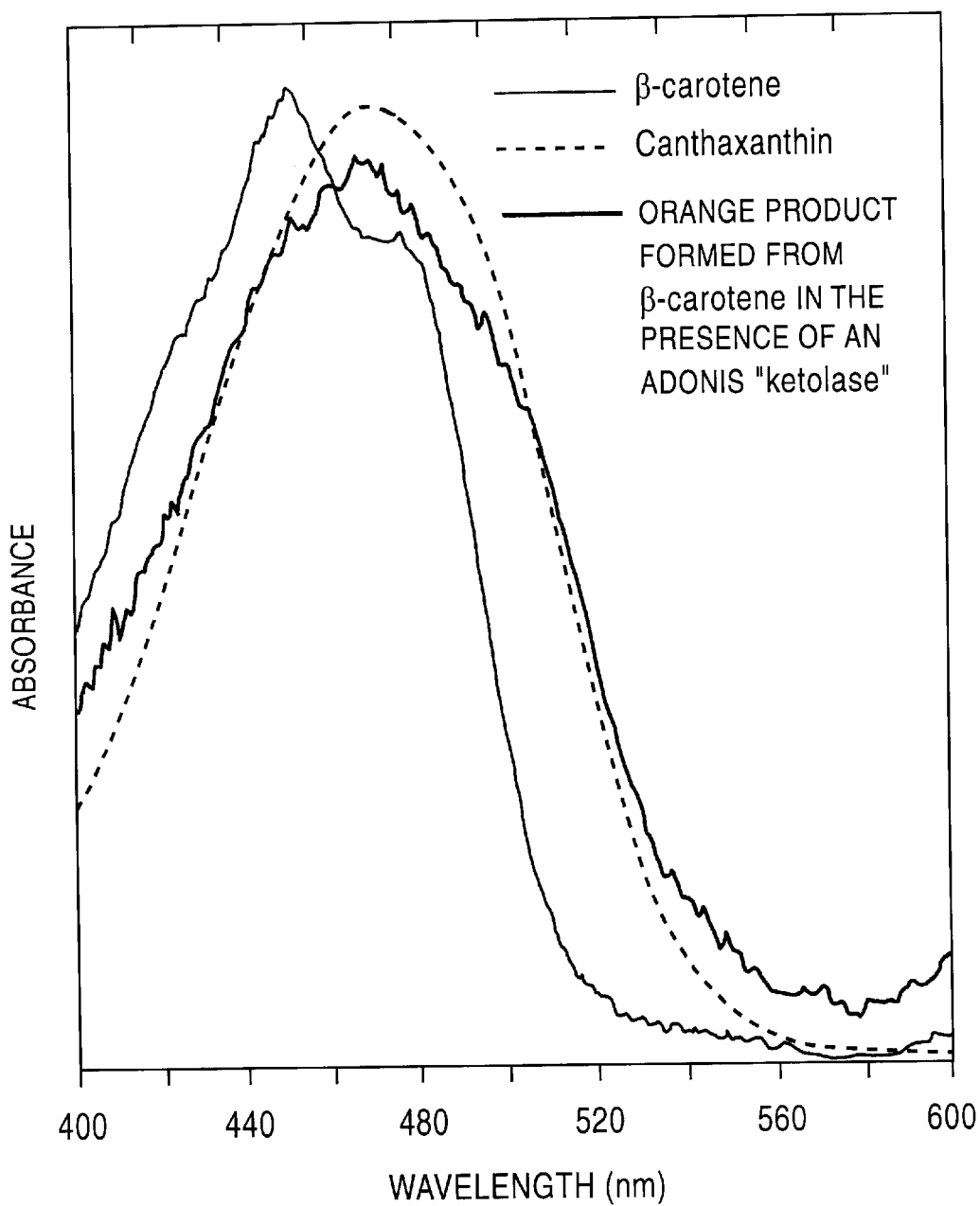
FIG. 4 illustrates the absorption spectrum of one of the orange carotenoids produced from b-carotene via the action of the Adonis ketolases and makes clear the similarity of the spectrum to that of canthaxanthin. Absorption spectra (in acetone) of β-carotene, canthaxanthin and an unknown orange product (orange band #1; the lower orange band in the first lane of FIG. 3) extracted from cultures after introduction of the *Adonis aestivalis* keto1 cDNA (SEQ ID NO: 1) in cells of *E. coli* that otherwise produce and accumulate β-carotene. The absorption spectrum of the unknown resembles that of canthaxanthin but the compound migrates to a position below echinenone on RP18 TLC plates developed with a mobile phase of methanol:acetone (1:1 by volume). The absorption spectrum of orange band #2 also is similar to that of canthaxanthin but it migrates more rapidly than canthaxanthin indicating that it is probably a more polar compound.

The products produced by the ketolases of the invention which have been expressed in a β-carotene-accumulating strain of *Eschericia coli* have not yet been identified. As many as 5 or 6 different colored bands, in addition to the substrate β-carotene, may readily be discerned by $C_{18}$ TLC separation (see FIG. 3). To provide appropriate standards to assist in identification, an *H. pluvialis* ketolase and an Arabidopsis β-carotene hydroxylase were separately introduced into the β-carotene-accumulating *E. coli* to produce echinenone (3-keto-β,β-carotene) and canthaxanthin (3,3'-diketo-β,β-carotene) or β-cryptoxanthin (4-hydroxy-β,β-carotene) and zeaxanthin (4,4'-dihydroxy-β,β-carotene). None of the compounds formed in the presence of the ketolases of the invention (no difference was observed in products formed in the presence of the two different nucleic acid sequences of the invention) both migrate in the TLC system and have the absorption spectrum expected for echinenone, canthaxanthin, β-cryptoxanthin, or zeaxanthin. Two of the colored TLC bands produced in the presence of the Adonis ketolase cDNAs are orange in color. Orange band #1 has an absorption spectrum similar to that of canthaxanthin (see FIG. 4) but migrates in a position that indicates a polarity intermediate to echinenone and β-carotene. Orange band #2 also has an absorption spectrum like that of canthaxanthin but migrates in a position that indicates a polarity intermediate to canthaxanthin and zeaxanthin (see FIG. 3). The absorption spectra and TLC results suggest that the two orange products could be desaturated at the 3–4 positions of both rings (3,4,-didehydro; see FIG. 2). Orange band #1 (see FIG. 3) might then be 3,4,3',4'-tetradehydro-β,β-carotene. To substantially affect the absorption spectrum of the substrate β-carotene, any modifications very likely involve a carbon that lies in conjugation with the conjugated chain of carbon-carbon double bonds that constitute the chromophore (Goodwin, 1980; *The Biochemistry of the Carotenoids*, volume I; $2^{nd}$ edition, Chapman and Hall). For the spectra obtained, only the carbons at the number 4 position of the two rings appear to be plausible locations for modification. The multitude and TLC migrations of the yellow and orange products produced from the symmetrical β-carotene, however, also indicates that the enzymes of the invention carry out more than a single type of reaction. The apparent homology of the ketolases of the invention to the Arabidopsis β-carotene hydroxylase would suggest that compounds with a hydroxyl at the 3 and/or 4 positions of one or both rings are another possible outcome (see FIG. 2). In fact, such compounds have been identified in Adonis (see above), and it has long been conjectured that a hydroxyl at position 4 is an intermediate in the formation of the 4-keto (e.g. crustaxanthin, a 3,3',4,4' tetrahydroxy carotenoid that might be a precursor for astaxanthin in the exoskeleton of the lobster). The histidine motifs and secondary structure in common to the hydroxylase and ketolase enzymes are characteristics of a large group of di-iron oxygenases whose members also include examples of desaturases (J. Shanklin, 1998, *Ann. Rev. Plant Physiol. Plant Mol. Biol.*), therefore a 3–4 desaturation (and/or perhaps a 2–3 desaturation in one or more of the yellow compounds) would also seem a plausible outcome.

To summarize the results of this example for the Adonis ketolases of the invention, a number of different carotenoids, including two with ketocarotenoid-like spectra, are produced from β-carotene via the action of the products of either of the two different nucleic acids of the invention. These orange compounds appear to be the major products. Truncation and fusion of the cDNAs to a stronger promoter in the vector pTrcHis (Invitrogen) was detrimental to growth of *E. coli* but did result in improved yield of the most polar orange product (orange band #2 in FIG. 3). Introduction of a cyanobacterial ferredoxin did not change the yield or relative amounts of the various products. Without being bound by theory, it may be that the ketocarotenoids produced in flower petals of Adonis actually include the as yet unidentified orange compounds that are produced in *E. coli* using the nucleic acids of the invention.

EXAMPLE 2

Substrate Specificity of the Adonis Ketolases

Carotenoids with ε rings are common in plants. The ε ring differs from the b ring only in the position of the double bond within the ring (FIG. 2). The ε ring is reported to be a poor substrate for the Arabidopsis b-carotene hydroxylase (Sun et al., 1996). The Adonis ketolase cDNAs were introduced into strains of *E. coli* engineered (Cunningham et al., 1996) to accumulate carotenoids with one or two ε rings (d-carotene and ε-carotene), or the acyclic carotenoid lycopene. TLC analysis of acetone extracts revealed that these carotenoids were not modified by the Adonis ketolases. as indicated by a lack of any new products formed. Products produced in *E. coli* engineered to accumulate zeaxanthin (Sun et al., 1996) appeared to be the same as for β-carotene accumulating cultures indicating that a 3-OH is likely to be one of the functional groups introduced to the b ring by the Adonis ketolases. The more polar orange band produced from b-carotene through the action of the Adonis ketolases (e.g., orange band 2 in FIG. 3), therefore, could very well be 3,3'-dihydroxy-3,4,3',4'-tetradehydro-b,b-carotene.

The references cited in the application, along with the following references, are incorporated by reference:

Bouvier F, et al. (1998) Xanthophyll biosynthesis: molecular and functional characterization of carotenoid hydroxylases from pepper fruits (Capsicum annuum L.). Biochim Biophys Acta. 1391:320–8

Breitenbach J, et al. (1996) Expression in Escherichia coli and properties of the carotene ketolase from Haematococcus pluvialis. FEMS Microbiol Lett. 140:241–6

Cunningham F X Jr, Gantt E (1998) Genes and enzymes of carotenoid biosynthesis in plants. Ann Rev Plant Physiol Plant Mol Biol 49: 557–583

Fernandez-Gonzalez B, et al. (1997) A new type of asymmetrically acting beta-carotene ketolase is required for the synthesis of echinenone in the cyanobacterium Synechocystis sp. PCC 6803. J Biol Chem. 272:9728–33

Fraser P D, et al. (1997) In vitro characterization of astaxanthin biosynthetic enzymes. J Biol Chem. 1997272:6128–35

Fraser P D, et al. (1998) Enzymic confirmation of reactions involved in routes to astaxanthin formation, elucidated using a direct substrate in vitro assay. Eur J Biochem. 252:229–36

Harker M, et al. (1997) Biosynthesis of ketocarotenoids in transgenic cyanobacteria expressing the algal gene for beta-C-4-oxygenase, crtO. FEBS Lett. 404:129–34

Kajiwara S, et al. (1995) Isolation and functional identification of a novel cDNA for astaxanthin biosynthesis from *Haematococcus pluvialis*, and astaxanthin synthesis in *Escherichia coli*. Plant Mol Biol. 29:343–52

Lotan T, et al. (1995) Cloning and expression in *Escherichia coli* of the gene encoding beta-C-4-oxygenase, that converts beta-carotene to the ketocarotenoid canthaxanthin in *Haematococcus pluvialis*. FEBS Lett. 364:125–8

Misawa N, et.al. (1995) Canthaxanthin biosynthesis by the conversion of methylene to keto groups in a hydrocarbon beta-carotene by a single gene. Biochem Biophys Res Commun.209:867–76

Misawa N, et al. (1995) Structure and functional analysis of a marine bacterial carotenoid biosynthesis gene cluster and astaxanthin biosynthetic pathway proposed at the gene level. J Bacteriol. 177:6575–84

Miura Y, et al. (1998) Production of the carotenoids lycopene, beta-carotene, and astaxanthin in the food yeast *Candida utilis*. Appl Environ Microbiol. 64:1226–9

Shanklin J, et al. (1997) Mossbauer studies of alkane omega-hydroxylase: evidence for a diiron cluster in an integral-membrane enzyme. Proc Natl Acad Sci U S A. 94:2981–6

Shanklin J, Cahoon E B (1998) Desaturation and related modifications of fatty acids. Ann Rev Plant Physiol Plant Mol Biol 49: 611–641

Wang C W, et al. Engineered isoprenoid pathway enhances astaxanthin production in *Escherichia coli*. Biotechnol Bioeng. Jan. 20, 1999; 62(2):235-41.

I claim:

1. A method of producing a ketocarotenoid in a host cell, the method comprising
   inserting into the host cell a vector comprising a heterologous nucleic acid sequence which encodes for a protein having ketolase enzyme activity and has the nucleic acid sequence of SEQ ID NO: 1 or 3, wherein the heterologous nucleic acid sequence is operably linked to a promoter; and
   expressing the heterologous nucleic acid sequence, thereby producing the ketocarotenoid.

2. The method of claim 1, wherein the host cell is selected from the group consisting of a bacterial cell, an algal cell and a plant cell.

3. A method of producing a ketocarotenoid in a host cell, the method comprising
   inserting into the host cell a vector comprising a heterologous nucleic acid sequence which encodes for a protein having ketolase enzyme activity and has a sequence which encodes the amino acid sequence of SEQ ID NO: 2 or 4, wherein the heterologous nucleic acid sequence is operably linked to a promoter; and
   expressing the heterologous nucleic acid sequence, thereby producing the ketocarotenoid.

4. The method of claim 3, wherein the host cell is selected from the group consisting of a bacterial cell, an algal cell and a plant cell.

5. A method of modifying the production of carotenoids in a host cell, relative to an untransformed host cell, the method comprising
   inserting into a host cell which already produces carotenoids a vector comprising a heterologous nucleic acid sequence which encodes for a protein having ketolase enzyme activity and has the nucleic acid sequence of SEQ ID NO: 1 or 3, wherein the heterologous nucleic acid sequence is operably linked to a promoter; and
   expressing the heterologous nucleic acid sequence in the host cell to modify the production of the carotenoids in the host cell, relative to an untransformed host cell.

6. The method of claim 5, wherein the host cell is selected from the group consisting of a bacterial cell, an algal cell and a plant cell.

7. A method of modifying the production of carotenoids in a host cell, relative to an untransformed host cell, the method comprising
   inserting into a host cell which already produces carotenoids a vector comprising a heterologous nucleic acid sequence which encodes for a protein having ketolase enzyme activity and has a sequence which encodes the amino acid sequence of SEQ ID NO: 2 or 4, wherein the heterologous nucleic acid sequence is operably linked to a promoter; and
   expressing the heterologous nucleic acid sequence in the host cell to modify the production of the carotenoids in the host cell, relative to an untransformed host cell.

8. The method of claim 7, wherein the host cell is selected from the group consisting of a bacterial cell, an algal cell and a plant cell.

9. A purified nucleic acid sequence which encodes for a protein having ketolase enzyme activity and has the nucleic acid sequence of SEQ ID NO: 1.

10. A purified nucleic acid sequence which encodes for a protein having ketolase enzyme activity and has the nucleic acid sequence of SEQ ID NO: 3.

11. A purified nucleic acid sequence which encodes for a protein having ketolase enzyme activity and has a sequence which encodes the amino acid sequence of SEQ ID NO: 2.

12. A purified nucleic acid sequence which encodes for a protein having ketolase enzyme activity and has a sequence which encodes the amino acid sequence of SEQ ID NO: 4.

13. A vector which comprises the nucleic acid sequence of any one of claims 9–12, wherein the nucleic acid sequence is operably linked to a promoter.

14. A host cell which is transformed with the vector of claim 13.

15. The host cell of claim 14, wherein the host cell is selected from the group consisting of a bacterial cell, an algal cell and a plant cell.

16. The host cell of claim 14, wherein the host cell is a photosynthetic cell.

17. The host cell of claim 14, wherein the host cell contains a ketocarotenoid.

18. The host cell of claim 14, wherein the host cell contains modified levels of carotenoids, relative to an untransformed host cell.

19. A purified ketolase enzyme comprising the amino acid sequence of SEQ ID NO: 2.

20. A purified ketolase enzyme comprising the amino acid sequence of SEQ ID NO: 4.

* * * * *